(12) United States Patent
Behdad et al.

(10) Patent No.: US 11,058,487 B2
(45) Date of Patent: Jul. 13, 2021

(54) MICROWAVE ABLATION ANTENNA SYSTEM WITH REFLECTOR AND SLOT

(71) Applicant: Wisconsin Alumni Research Foundation, Madison, WI (US)

(72) Inventors: Nader Behdad, Oregon, WI (US); Susan C. Hagness, Madison, WI (US); Yahya Mohtashami, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 893 days.

(21) Appl. No.: 15/454,170

(22) Filed: Mar. 9, 2017

(65) Prior Publication Data

US 2018/0261922 A1 Sep. 13, 2018

(51) Int. Cl.
*A61B 18/18* (2006.01)
*A61B 18/00* (2006.01)

(52) U.S. Cl.
CPC ............ *A61B 18/1815* (2013.01); *A61B 2018/00577* (2013.01); *A61B 2018/00785* (2013.01); *A61B 2018/1853* (2013.01)

(58) Field of Classification Search
CPC ...... A61B 18/1815; A61B 2018/00577; A61B 2018/00785; A61B 2018/1853
See application file for complete search history.

(56) References Cited

U.S. PATENT DOCUMENTS

| | | | |
|---|---|---|---|
| 5,300,099 A | 4/1994 | Rudie | |
| 5,683,382 A | 11/1997 | Lenihan | |
| 6,051,018 A | 4/2000 | Larsen | |
| 6,245,062 B1 * | 6/2001 | Berube | A61B 18/14 606/33 |
| 6,471,696 B1 * | 10/2002 | Berube | A61B 18/1492 606/33 |
| 7,226,446 B1 * | 6/2007 | Mody | A61B 18/18 606/33 |
| 2006/0189973 A1 * | 8/2006 | van der Weide | A61B 18/18 606/33 |

(Continued)

OTHER PUBLICATIONS

Nwoye et al., Finite Element Analysis of Single Slot Antenna for Microwave Tumor Ablation, IOSR Journal of Applied Physics, vol. 5, Issue 6, Jan. 2014, pp. 55-62.

(Continued)

*Primary Examiner* — Daniel W Fowler
(74) *Attorney, Agent, or Firm* — Bell & Manning, LLC

(57) ABSTRACT

An antenna system is provided that includes a coaxial cable, an antenna, a reflector wall, and a slot wall. The reflector wall is formed of a conductive material connected to a conductive shield to extend in an axial direction, is separated from an antenna conductor by a second dielectric material in a radial direction relative to the antenna conductor, and partially surrounds the antenna conductor in the radial direction from a first angle to a second angle when projected into a radial plane. The slot wall is formed through a portion of the conductive shield to expose a dielectric material from a third angle to a fourth angle when projected into the radial plane, is formed on a first side relative to a base. The first angle, the second angle, the third angle, and the fourth angle are defined relative to a common axis parallel to the radial plane.

20 Claims, 18 Drawing Sheets

(56) References Cited

U.S. PATENT DOCUMENTS

| | | | | |
|---|---|---|---|---|
| 2010/0125269 | A1* | 5/2010 | Emmons | A61B 18/1815 606/33 |
| 2010/0217252 | A1* | 8/2010 | Rossetto | A61B 18/18 606/33 |
| 2010/0305561 | A1* | 12/2010 | Prakash | A61B 18/18 606/33 |
| 2011/0040300 | A1* | 2/2011 | Brannan | A61B 18/18 606/41 |
| 2014/0358140 | A1 | 1/2014 | Emmons | |
| 2015/0250540 | A1 | 9/2015 | Behdad | |

OTHER PUBLICATIONS

Mohtashami et al., A Minimally-Invasive Integrated Slot/Monopole Antenna for Generating Anisotropic Microwave Ablation Zones, IEEE International Symposium on Antennas and Propagation/USNC-URSI National Radio Science meeting, Jun. 26, 2016, Puerto Rico.

Mohtashami et al., A Minimally-Invasive Integrated Slot/Monopole Antenna for Generating Anisotropic Microwave Ablation Zones, Conference slides, IEEE International Symposium on Antennas and Propagation/USNC-URSI National Radio Science meeting, Jun. 26, 2016, Puerto Rico.

Açýkgöz et al., A Novel Microwave Coaxial Slot Antenna for Liver Tumor Ablation, Advanced Electromagnetics, vol. 3, No. 1, Apr. 2014.

Kitchin et al., Microwave ablation of malignant hepatic tumours: Intraperitoneal fluid instillation prevents collateral damage and allows more aggressive case selection, Int. J. Hyperthermia, vol. 30, No. 5, Aug. 20, 2014, pp. 299-305.

Oshima et al., Simultaneous microwave ablation using multiple antennas in explanted bovine livers: relationship between ablative zone and antenna, Radiation Medicine, vol. 26, No. 7, Aug. 2008, pp. 408-414.

Brace et al., Microwave ablation with multiple simultaneously powered small-gauge triaxial antennas: results from an in vivo swine liver model, Radiology, vol. 244, No. 1, Jul. 2007, pp. 151-156.

McWilliams et al., A Directional Interstitial Antenna for Microwave Tissue Ablation: Theoretical and Experimental Investigation, IEEE Trans. Biomed. Eng., vol. 62, No. 9, Sep. 2015, pp. 2144-2150.

Luyen et al., A balun-free helical an-tenna for minimally-invasive microwave ablation, IEEE Trans. Antennas Propag., vol. 63, No. 3, Mar. 2015, pp. 959-965.

Saito et al., Clinical trials of interstitial microwave hyperthermia by use of coaxial-slot antenna with two slots, IEEE Trans. Microw. Theory Tech., vol. 52, No. 8, Aug. 2004, pp. 1987-1991.

International Search Report and Written Opinion for PCT/US2018/067469, dated Apr. 18, 2019.

* cited by examiner

MICROWAVE ABLATION ANTENNA SYSTEM WITH REFLECTOR AND SLOT

REFERENCE TO GOVERNMENT RIGHTS

This invention was made with government support under ECCS1406090 awarded by the National Science Foundation. The government has certain rights in the invention.

BACKGROUND

Microwave ablation (MWA) is a form of thermal ablation used in interventional radiology to treat cancer. MWA uses electromagnetic waves in the microwave energy spectrum (300 megahertz to 300 gigahertz) to produce tissue-heating effects, i.e., to heat tumors to cytotoxic temperatures. MWA is generally used for minimally invasive treatment and/or palliation of solid tumors in patients. MWA offers several advantages over other ablation technologies such as radiofrequency (RF) and cryoablation including higher temperatures than RF, larger ablation zone volumes, shorter ablation times, and better ablation performance near arteries, which act as heat sinks. Selective delivery of energy to the prescribed tissue volume (i.e. the tumor and its margins) is achieved by means of interstitial placement of a microwave antenna directly into the tumor. Current MWA technology may be employed either laparoscopically or percutaneously, and thus, is considered to be minimally invasive. However, the extent to which MWA is minimally invasive depends on a length and a diameter of the interstitial microwave antenna.

Most MWA antennas are axisymmetric in nature and as a result, produce axisymmetric ablation zones in homogenous tissue. However, these rotationally symmetric ablation zones prevent successful ablation of tumors in certain scenarios. For example, a direct access path to a target tumor may be blocked by a vital organ or a vital organ that should not be ablated may be in proximity to the targeted ablation zone. Clinical examples of these cases are hepatic tumors close to the bowel or diaphragm, tumors on the periphery of lungs, renal tumors in the vicinity of bowel, breast tumors close to the chest wall, etc.

SUMMARY

An antenna system is provided that includes, but is not limited to, a coaxial cable, an antenna, a reflector wall, and a slot wall. The coaxial cable includes, but is not limited to, a center conductor extending a length of the coaxial cable, a dielectric material surrounding the center conductor along the length of the coaxial cable, and a conductive shield surrounding the dielectric material along the length of the coaxial cable. The antenna includes, but is not limited to, a base connected to the center conductor on a first side and an antenna conductor connected to the base on a second side opposite the first side. The antenna conductor extends in an axial direction from the second side of the base, wherein a radial plane through the base is perpendicular to the axial direction. The reflector wall is formed of a conductive material connected to the conductive shield to extend in the axial direction. The reflector wall is separated from the antenna conductor by a second dielectric material in a radial direction relative to the antenna conductor, wherein the reflector wall partially surrounds the antenna conductor in the radial direction from a first angle to a second angle when projected into the radial plane. The slot wall is formed through a portion of the conductive shield to expose the dielectric material from a third angle to a fourth angle when projected into the radial plane, wherein the slot wall is formed on the first side relative to the base. The first angle, the second angle, the third angle, and the fourth angle are defined relative to a common axis parallel to the radial plane.

A microwave ablation system is provided that includes, but is not limited to, an antenna system, a signal generator, and a connector. The antenna system includes, but is not limited to, a coaxial cable, an antenna, a reflector, and a slot wall. The coaxial cable includes, but is not limited to, a center conductor extending a length of the coaxial cable, a dielectric material surrounding the center conductor along the length of the coaxial cable, and a conductive shield surrounding the dielectric material along the length of the coaxial cable. The antenna includes, but is not limited to, a base connected to the center conductor on a first side and an antenna conductor connected to the base on a second side opposite the first side. The antenna conductor extends in an axial direction from the second side of the base, wherein a radial plane through the base is perpendicular to the axial direction. The reflector is formed of a conductive material connected to the conductive shield to extend in the axial direction. The reflector is separated from the antenna conductor by a second dielectric material in a radial direction relative to the antenna conductor. The reflector partially surrounds the antenna conductor in the radial direction from a first angle to a second angle when projected into the radial plane. The slot wall is formed through a portion of the conductive shield to expose the dielectric material from a third angle to a fourth angle when projected into the radial plane. The slot wall is formed on the first side relative to the base. The first angle, the second angle, the third angle, and the fourth angle are defined relative to a common axis parallel to the radial plane. The signal generator is configured to generate a signal at a selected operating frequency. The connector is configured to connect a second end of the coaxial cable opposite the base of the antenna to the signal generator to receive the generated signal.

Other principal features of the disclosed subject matter will become apparent to those skilled in the art upon review of the following drawings, the detailed description, and the appended claims.

BRIEF DESCRIPTION OF THE DRAWINGS

Illustrative embodiments of the disclosed subject matter will hereafter be described referring to the accompanying drawings, wherein like numerals denote like elements.

DETAILED DESCRIPTION

Figure 1:
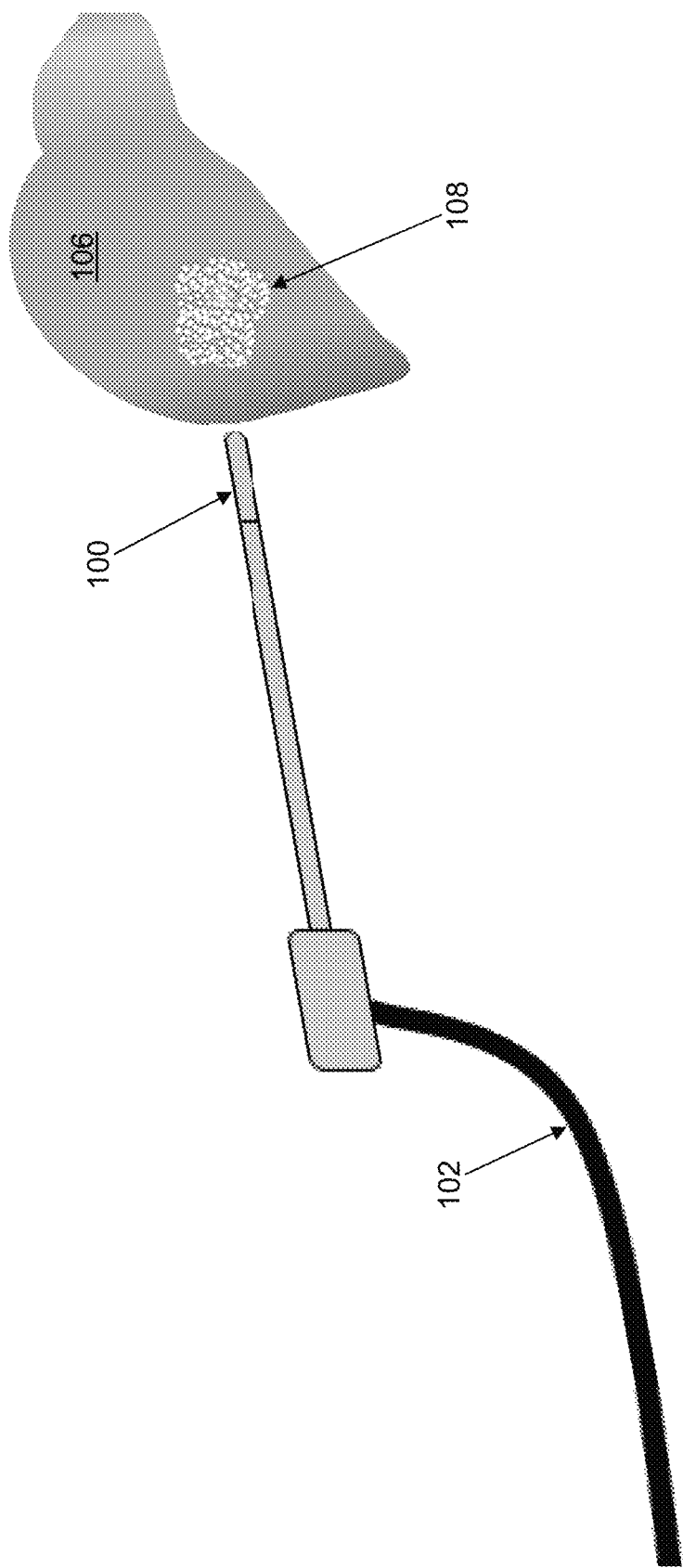
FIG. 1 depicts a microwave ablation (MWA) antenna system in accordance with an illustrative embodiment.

With reference to FIG. 1, a microwave ablation (MWA) antenna 100 is connected to and fed by a coaxial cable 102 that provides electromagnetic energy to antenna 100 at a selected operating frequency $f_0$. MWA can be used to provide thermal therapy for treatment of various types of cancer 108 in various tissue/organs 106. Tissue/organs 106 may include liver, kidney, lung, bone, etc. MWA uses microwave frequency in the range 300 megahertz (MHz) to 300 gigahertz (GHz), though the range from 915 MHz to 2.45 GHz is most commonly used. MWA can be used to elevate the temperature of cancerous tissues to cytotoxic levels (e.g. >50° Celsius (C)) that quickly results in cell death. Electromagnetic waves are introduced into cancerous tissues by inserting antenna 100 interstitially into the tumor or other cancerous tissue.

Figure 2:
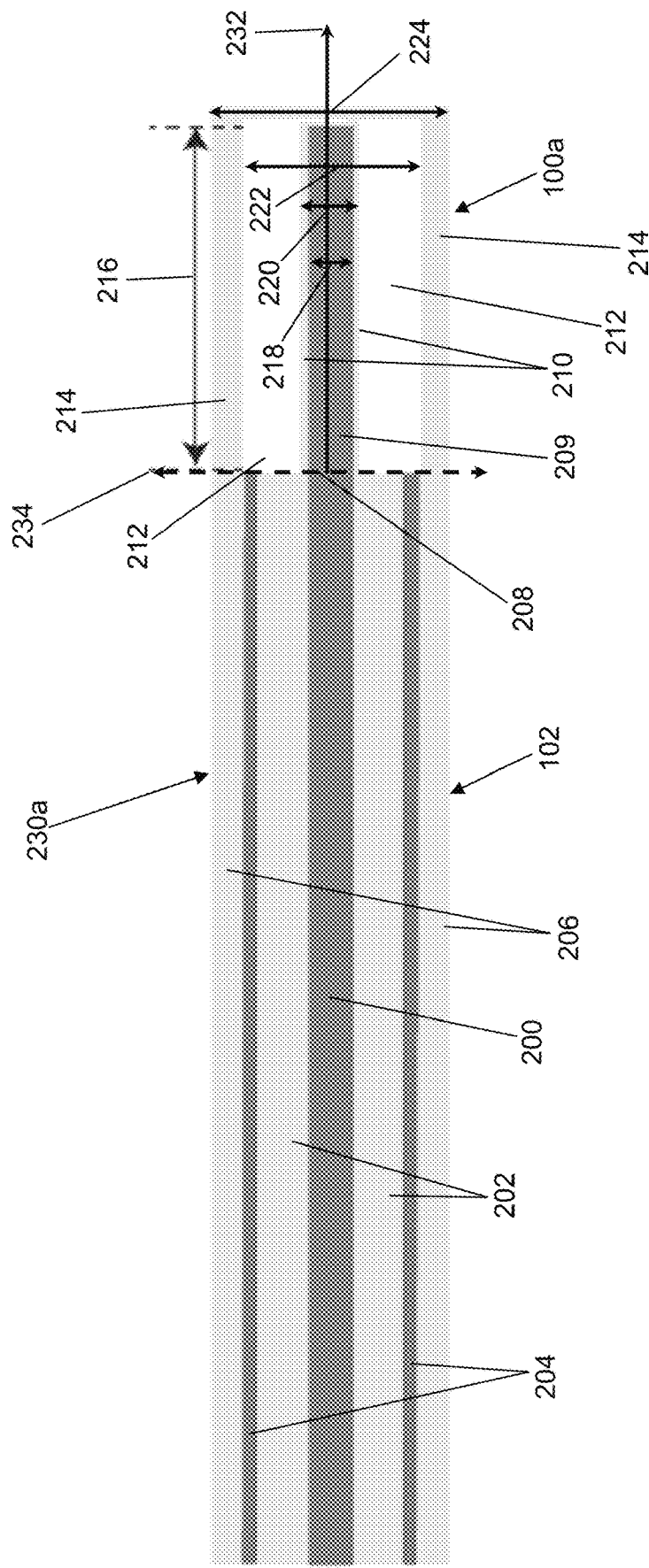
FIG. 2 depicts a side cross sectional view of a first MWA antenna for use in the MWA antenna system of FIG. 1 in accordance with an illustrative embodiment.

With reference to FIG. 2, a side cross-sectional view of a first antenna system 230a is shown in accordance with an illustrative embodiment. First antenna system 230a may include coaxial cable 102 and a first antenna 100a.

Coaxial cable 102 may include a center conductor 200 extending a length of coaxial cable 102, a dielectric material 202 surrounding center conductor 200 along the length of coaxial cable 102, a conductive shield 204 surrounding dielectric material 202 along the length of coaxial cable 102, and an insulating jacket 206 surrounding conductive shield 204 along the length of coaxial cable 102. Center conductor 200 is generally circular and may be formed of a solid conductive material such as copper plated steel wire, silver plated steel wire, silver plated copper wire, silver plated copper clad steel wire, copper wire, copper clad aluminum wire, steel wire, etc. Coaxial cable 102 may have a variety of diameters. Dielectric material 102 may include foamed polyethylene, solid polyethylene, polyethylene foam, polytetrafluoroethylene, air, air space polyethylene, vacuum, etc. Conductive shield 204 may be formed of a solid or braided conductive material such as copper, steel, aluminum, silver plated copper, silver plated copper clad steel, etc. Insulating jacket 206 can be made from many different insulating materials such as polyvinyl chloride or another plastic material.

Coaxial cable 102 may be rigid, semi-rigid, or flexible. The characteristic impedance may be off the shelf and range between approximately 20 and approximately 125 ohms or be designed to have a selected characteristic impedance within, above, or below this range as understood by a person of skill in the art using various dielectric and conductive materials, diameters, and thicknesses.

First antenna 100a may be a monopole antenna. First antenna 100a may include a base 208 and an antenna conductor 209. Base 208 is connected to center conductor 200 on a first side and is a feed end of first antenna 100a. Antenna conductor 209 connects to base 208 on a second side opposite the first side. Antenna conductor 209 extends in an axial direction from the second side of base 208. A radial plane 234 can be defined through base 208 that is perpendicular to an axial direction 232. Axial direction 232 extends from a center of antenna conductor 209.

First antenna 100a is formed of a conductive material that may be the same material as and/or may be an extension of center conductor 200 of coaxial cable 102. As understood by a person of skill in the art, the wavelength of operation, $\lambda_0$, of first antenna 100a is defined as $\lambda_2 = c/f_0$, where c is the speed of light in an environment in which antenna 100 is used, such as a body tissue, and $f_0$ is a selected operating frequency of a signal carried by center conductor 200 of coaxial cable 102. For illustration, $f_0$ may be between 500 MHz and 30 GHz. The wavelength of operation, $\lambda_0$, is a wavelength at the selected operating frequency in a medium in which first antenna 100a is selected to operate. For example, the medium includes first antenna dielectric material 210, second antenna dielectric material 212, and third antenna dielectric material 214 and the body tissue in which first antenna 100a is used to perform MWA.

First antenna 100a may be formed of a straight section of conducting wire, of a plurality of helical turns, of a bent wire, etc. A cross section of first antenna 100a may be circular, square, elliptical, rectangular, etc. though it is typically circular when formed as an extension of center conductor 200 of coaxial cable 102. First antenna 100a has an antenna length 216 of approximately $0.252\lambda_0$ defined from radial plane 234. For example, antenna length 216 was selected as 9 millimeters (mm) to operate at 7 GHz in egg white. First antenna 100a has an antenna width 218 equal to 0.515 mm for coaxial cable 102 selected as 50-ohm (Ω) UT-085C semi-rigid cable. For illustration, antenna width 218 may be selected as $\leq 0.10\lambda_0$.

A first antenna dielectric material 210 may surround antenna conductor 209 along a length of antenna conductor 209. First antenna dielectric material 210 may be the same material as and/or may be an extension of dielectric material 202. A first antenna dielectric width 220 defines a cross section width of first antenna dielectric material 210 surrounding antenna conductor 209. A depth of first antenna dielectric material 210 is half of first antenna dielectric width 220 minus half of antenna width 218. For illustration, the depth of first antenna dielectric material 210 is 0.05 mm computed using 0.5*(0.615−0.515). For illustration, first antenna dielectric width 220 may be selected as ≤0.12$\lambda_0$. The depth of first antenna dielectric material 210 may be selected as ≤0.01$\lambda_0$.

A second antenna dielectric material 212 may surround first antenna dielectric material 210. A second antenna dielectric width 222 defines a cross section width of second antenna dielectric material 212 surrounding first antenna dielectric material 210. A depth of second antenna dielectric material 212 is half of second antenna dielectric width 222 minus half of first antenna dielectric width 220. For illustration, the depth of second antenna dielectric material 212 is 0.791 mm computed using 0.5*(2.197−0.615), and second antenna dielectric width 222 is 2.197 mm. The depth of second antenna dielectric material 212 may be selected as ≤0.16$\lambda_0$, and second antenna dielectric width 222 may be selected as ≤0.45$\lambda_0$.

A third antenna dielectric material 214 may surround second antenna dielectric material 212. Third antenna dielectric material 214 may be the same material as and/or may be an extension of insulating jacket 206. A third antenna dielectric width 224 defines a cross section width of third antenna dielectric material 214 surrounding second antenna dielectric material 212. A depth of third antenna dielectric material 214 is half of third antenna dielectric width 224 minus half of second antenna dielectric width 222. For illustration, the depth of third antenna dielectric material 214 is 0.3515 mm and third antenna dielectric width 224 is 2.9 mm. The depth of third antenna dielectric material 214 may be selected as ≤0.07$\lambda_0$, and third antenna dielectric width 224 may be selected as ≤0.6$\lambda_0$.

For example, first antenna dielectric material 210, second antenna dielectric material 212, and third antenna dielectric material 214 may include foamed polyethylene, solid polyethylene, polyethylene foam, polytetrafluoroethylene, air, air space polyethylene, vacuum, alumina, etc. For illustration, the dielectric materials may include any low loss dielectric materials having a permittivity relative to a vacuum within the range of 1-30. For illustration, first antenna dielectric material 210 and third antenna dielectric material 214 are polytetrafluoroethylene, and second antenna dielectric material 212 is air.

Figure 3:
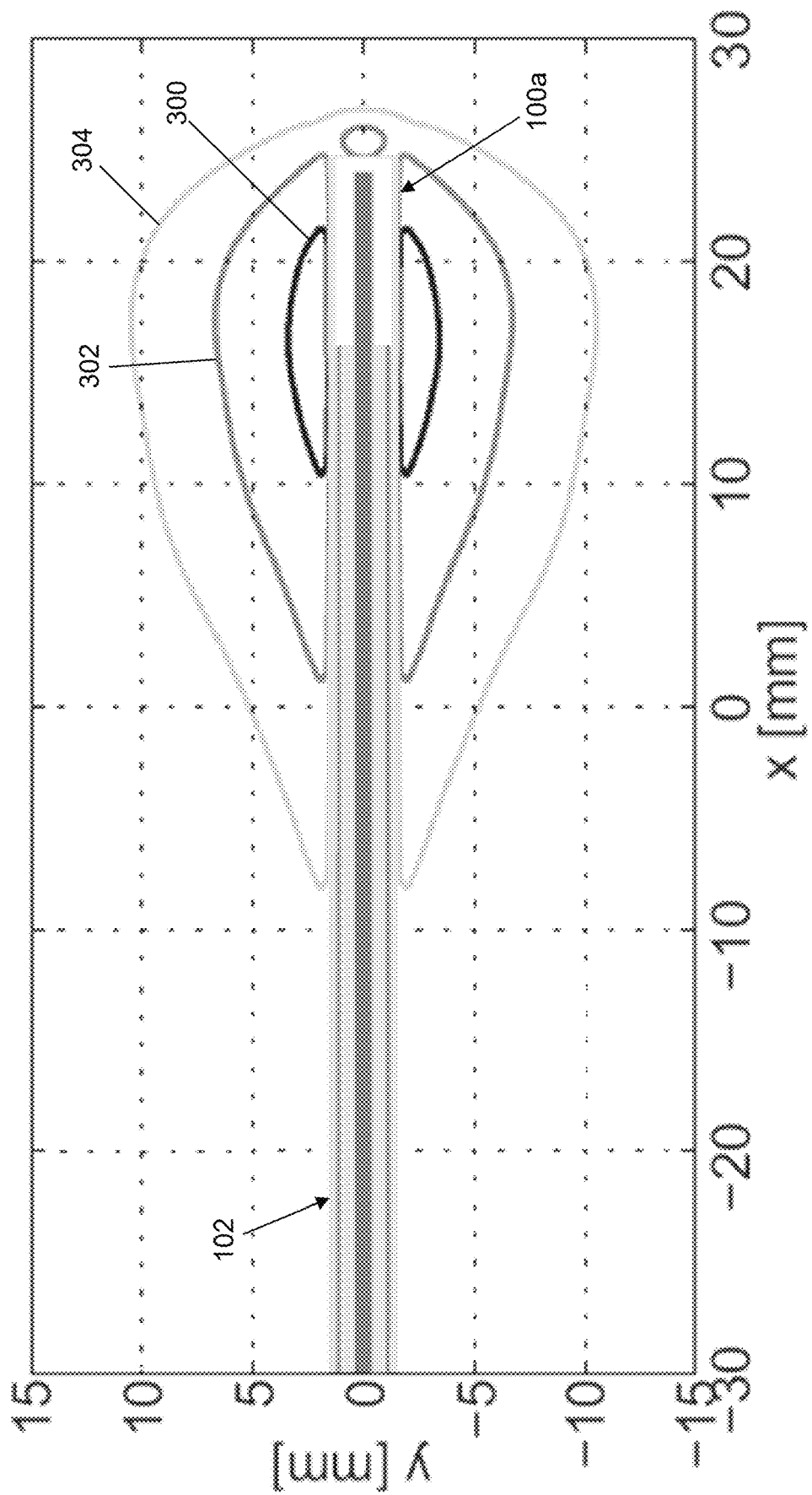
FIG. 3 shows a normalized specific absorption rate (SAR) pattern of the first MWA antenna of FIG. 2 in the x-y plane in accordance with an illustrative embodiment.

Referring to FIG. 3, a simulated specific absorption rate (SAR) pattern formed by first antenna 100a operating at 7 GHz is shown in accordance with an illustrative embodiment x-y plane, where y is in radial plane 234 and x is in axial direction 232. The SAR pattern was normalized to its associated maximum value. The simulated results assumed egg white. A −5 decibel (dB) curve 300 shows a SAR level reduced by 5 dB. A −15 dB curve 302 shows a SAR level reduced by 15 dB. A −25 dB curve 304 shows a SAR level reduced by 25 dB. First antenna 100a and coaxial cable 102 are shown for reference. First antenna 100a and coaxial cable 102 have an axisymmetric SAR pattern as is typical in MWA systems.

Figure 4:
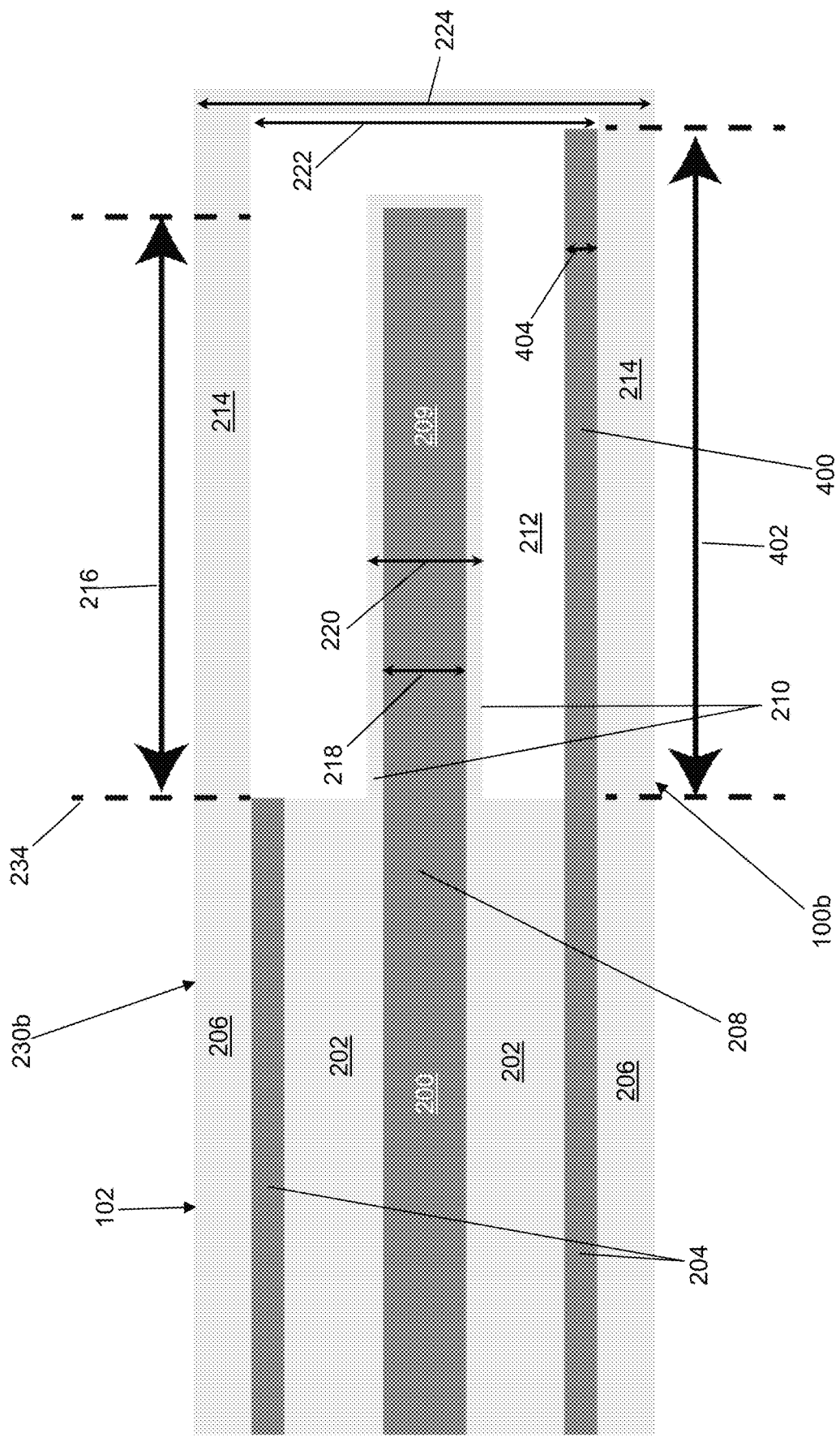
FIG. 4 depicts a side cross sectional view of a second MWA antenna for use in the MWA antenna system of FIG. 1 in accordance with an illustrative embodiment.
Figure 5:
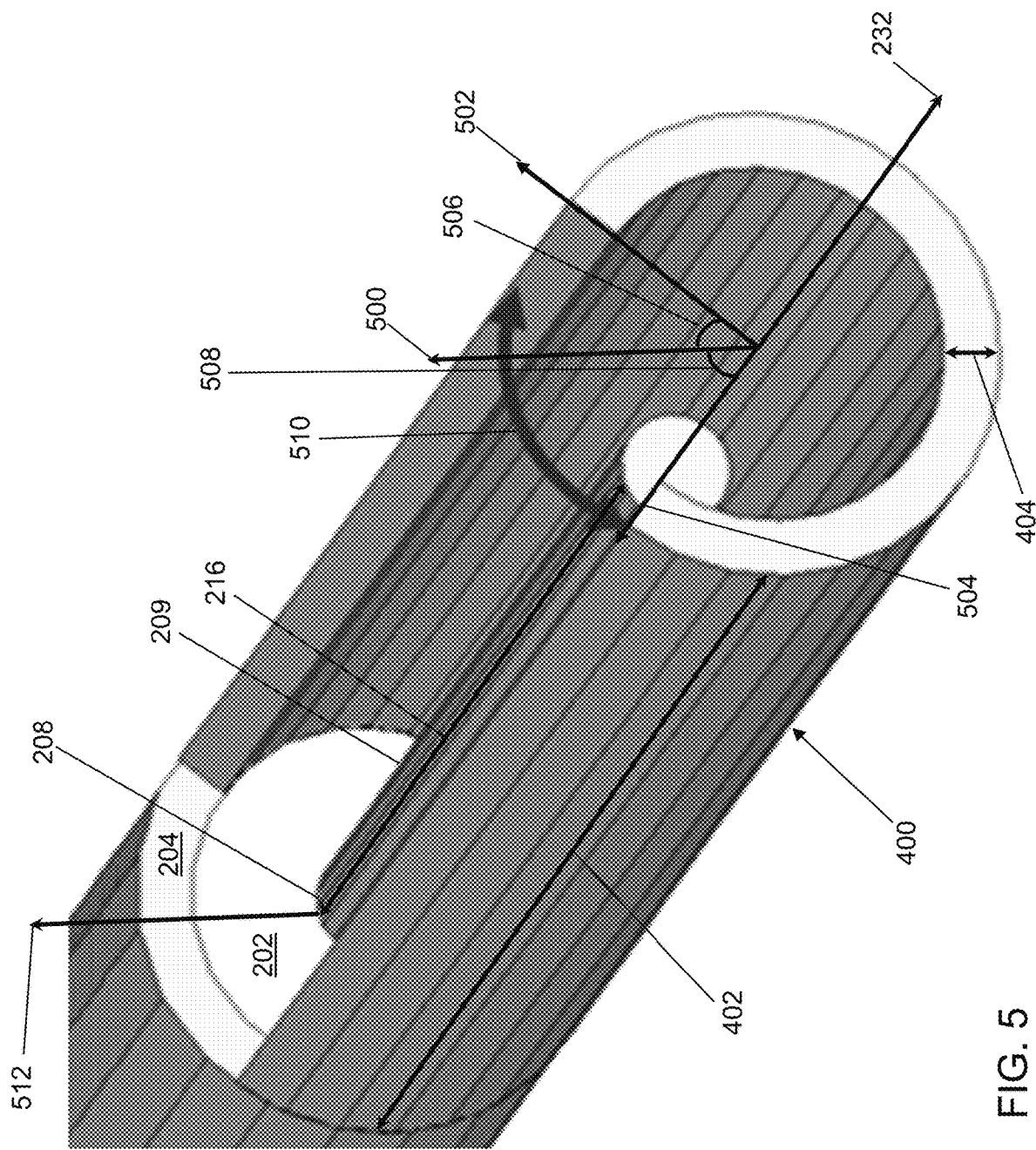
FIG. 5 depicts a perspective view of the second MWA antenna of FIG. 4 in accordance with an illustrative embodiment.

With reference to FIG. 4, a side cross-sectional view of a second antenna system 230b is shown in accordance with an illustrative embodiment. With reference to FIG. 5, a perspective view of second antenna system 230b is shown in accordance with an illustrative embodiment. Second antenna system 230b may include coaxial cable 102 and a second antenna 100b. Second antenna 100b includes first antenna 100a and a reflector wall 400.

Reflector wall 400 is formed of a conductive material that may be the same material as and/or may be an extension of conductive shield 204 of coaxial cable 102. Reflector wall 400 has a reflector length 402 of between approximately 0.25$\lambda_0$ and approximately 0.4$\lambda_0$ relative to radial plane 234 defined through base 208 of first antenna 100a. Reflector wall 400 has a reflector width 404 in radial plane 234. A y-axis 512 is perpendicular to axial direction 232 and is in radial plane 234. A z-axis (not shown) is perpendicular to y-axis 512 and to axial direction 232. Reflector length 402 in axial direction 232 is greater than or equal to antenna length 216 in axial direction 232. The z-axis and y-axis 512 define radial plane 234.

Reflector wall 400 is separated from antenna conductor 209 by second dielectric material 212 in a radial direction relative to a center of antenna conductor 209. Reflector wall 400 partially surrounds antenna conductor 209 in a radial direction from a first angle 506 to a second angle 508 when projected into radial plane 234. An up direction 500 is parallel to radial plane 234 and more specifically to y-axis 512 and extends from and is perpendicular to axial direction 232. First angle 506 is defined between up direction 500 and a first vector 502 that extends from axial direction 232 in radial plane 234 to a first edge wall of reflector wall 400. Second angle 508 is defined between up direction 500 and a second vector 504 that extends from axial direction 232 in radial plane 234 to a second edge wall of reflector wall 400. Up direction 500 is centered between first angle 502 and second angle 504. Reflector slot angle 510 defines an angle between first vector 502 and second vector 504. Reflector wall 400 forms a wall between first vector 502 and second vector 504 and defines a total angle of 360° minus reflector slot angle 510. In the illustrative embodiment of FIG. 5, reflector slot angle 510 is 90° and the total angle of reflector wall 400 is 270°.

For illustration, reflector length 402 was selected as 9 mm and antenna length 216 was selected as 7 mm to operate at 7 GHz in egg white. First antenna 100a has an antenna width 218 equal to 0.515 mm for coaxial cable 102 selected as 50-ohm (Ω) UT-085C semi-rigid cable.

Figure 6:
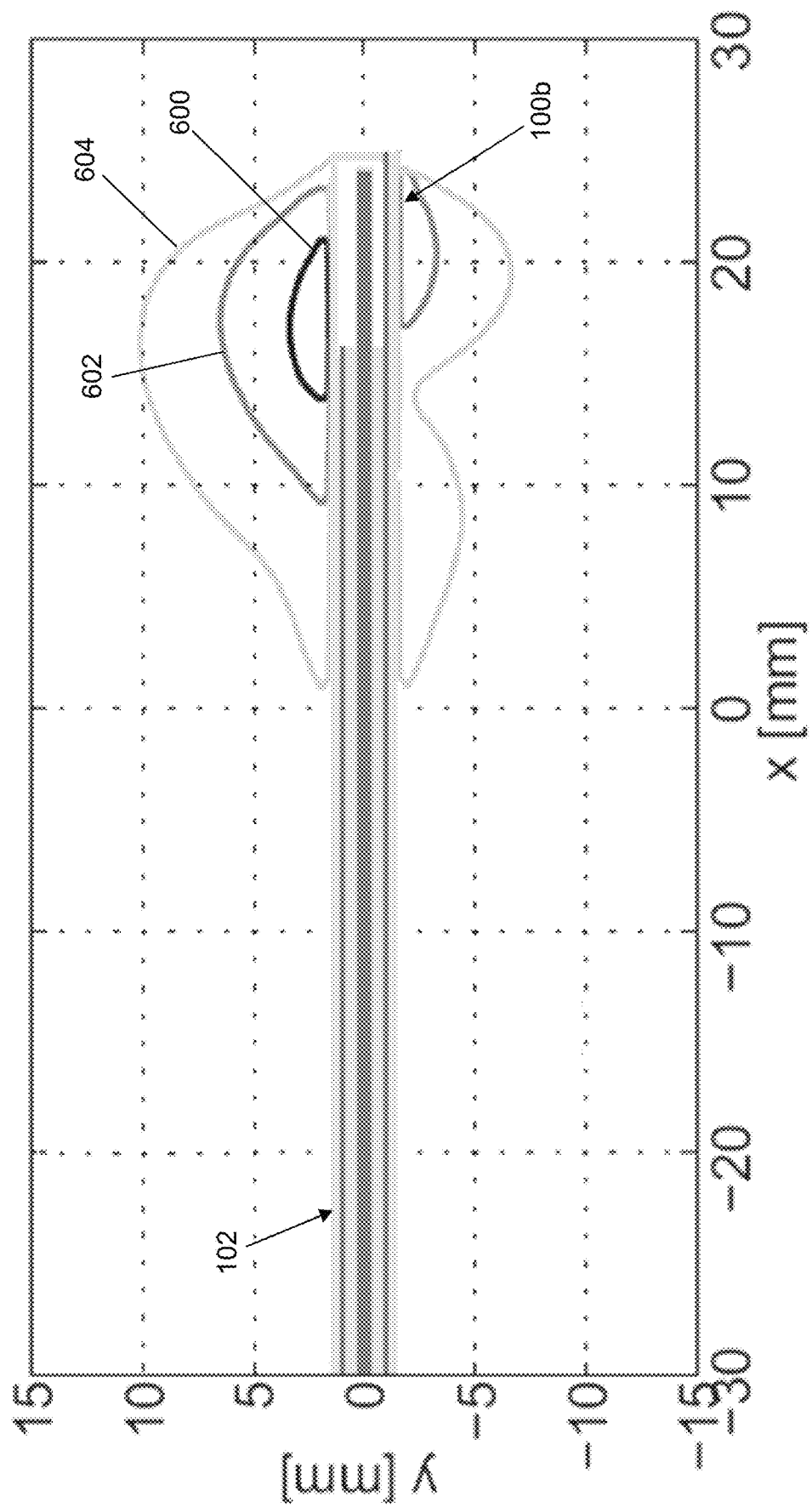
FIG. 6 shows a normalized SAR pattern of the MWA antenna of FIGS. 4 and 5 in the x-y plane in accordance with an illustrative embodiment.

Referring to FIG. 6, a simulated SAR pattern formed by second antenna 100b operating at 7 GHz is shown in accordance with an illustrative embodiment in the x-y plane, where y is in radial plane 234 and x is in axial direction 232. The SAR pattern was normalized to its associated maximum value. The simulated results assumed egg white. A −5 decibel (dB) curve 600 shows a SAR level reduced by 5 dB. A −15 dB curve 602 shows a SAR level reduced by 15 dB. A −25 dB curve 604 shows a SAR level reduced by 25 dB. Second antenna 100b and coaxial cable 102 are shown for reference. Second antenna 100b and coaxial cable 102 create an asymmetric SAR pattern with a decreased radiation in the direction of reflector wall 400.

Figure 7:
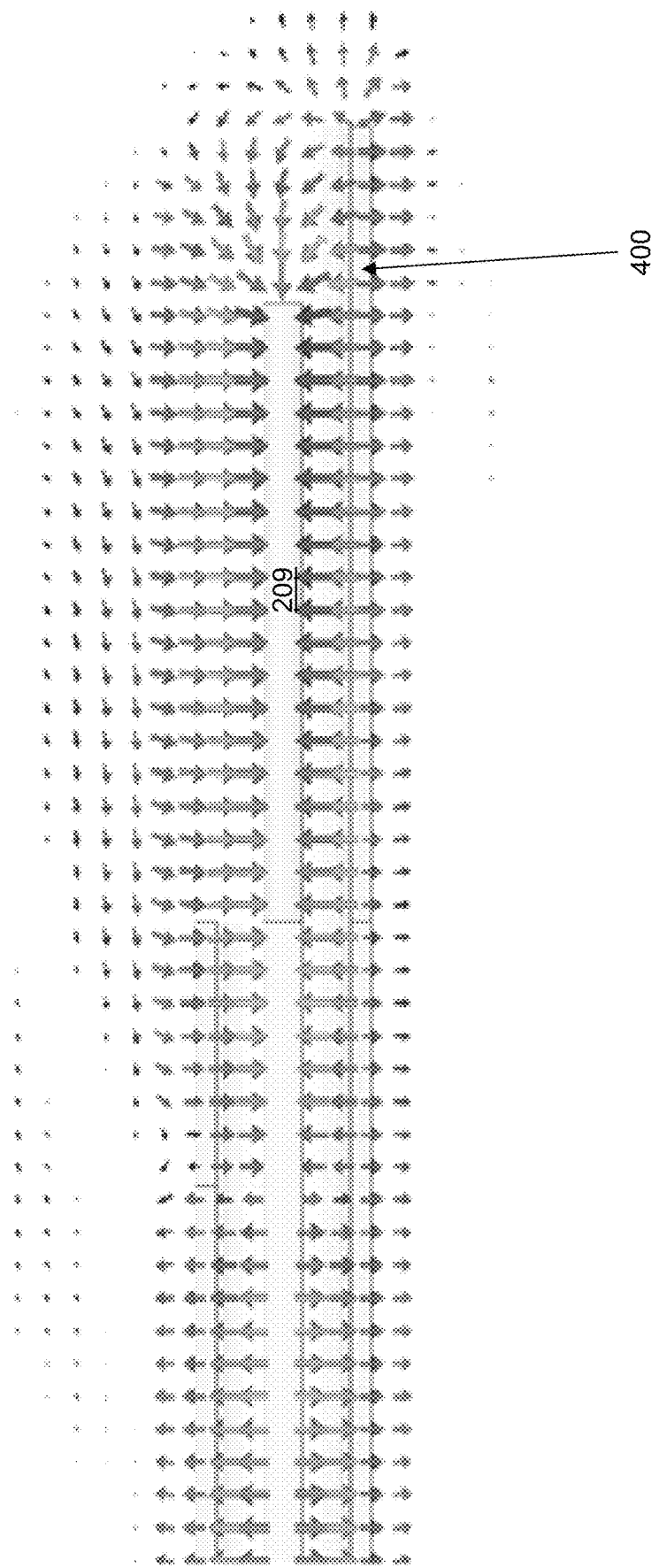
FIG. 7 shows a simulated electric field pattern of the MWA antenna system of FIGS. 4 and 5 in the x-y plane in accordance with an illustrative embodiment.

Referring to FIG. 7, a simulated electric field direction in a near field region formed by second antenna 100b operating at 7 GHz is shown in accordance with an illustrative embodiment in the x-y plane. The simulated electric field direction is shown using a normalized dB scale (with respect to its corresponding maximum value) for the electric field.

Figure 8:
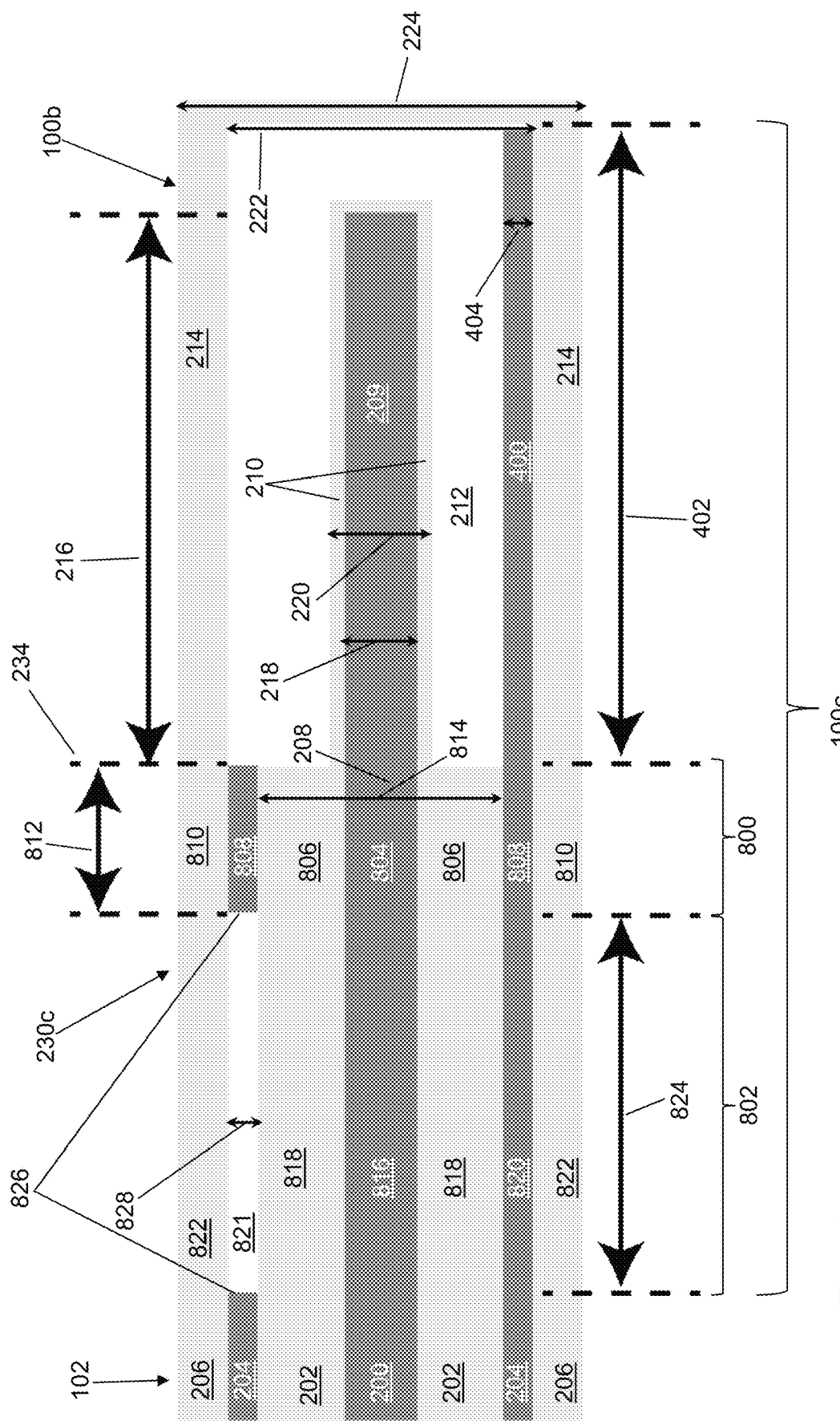
FIG. 8 depicts a side cross sectional view of a third MWA antenna for use in the MWA antenna system of FIG. 1 in accordance with an illustrative embodiment.
Figure 9:
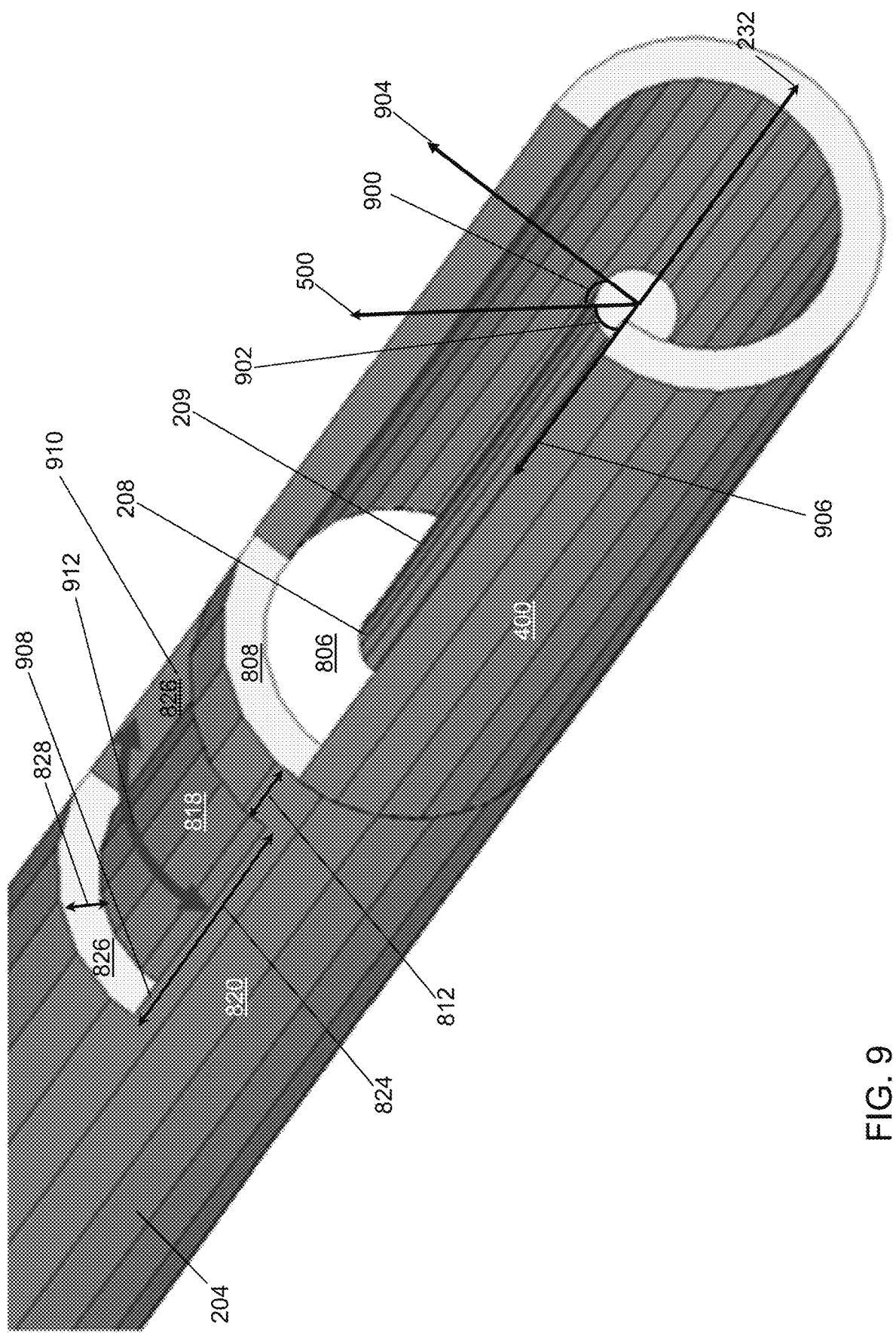
FIG. 9 depicts a perspective view of the third MWA antenna of FIG. 8 in accordance with an illustrative embodiment.

With reference to FIG. 8, a side cross-sectional view of a third antenna system 230c is shown in accordance with an illustrative embodiment. With reference to FIG. 9, a perspective view of third antenna system 230c is shown in accordance with an illustrative embodiment. Third antenna system 230c may include coaxial cable 102 and a third antenna 100c. Third antenna 100c includes second antenna 100b, a coaxial cable section 800, and a slot wall section 802.

Coaxial cable section 800 may be formed of a section of coaxial cable 102 having a coaxial section length 812. Coaxial section length 812 may be defined from radial plane 234 to a closest end of slot wall section 802 and may be selected from a range defined between and inclusive of $0.004\lambda_0$ and $0.1\lambda_0$. Coaxial cable section 800 may include a coax section center conductor 804 extending a length of coaxial cable section 800, a coax section dielectric material 806 surrounding coax section center conductor 804 extending a length of coaxial cable section 800, a coax section conductive shield 808 surrounding coax section dielectric material 806 along the length of coaxial cable section 800, and a coax section insulating jacket 810 surrounding coax section conductive shield 808 along the length of coaxial cable section 800.

A coax section dielectric material width 814 defines a cross section width of coax section dielectric material 806 surrounding coax section center conductor 804. A depth of coax section dielectric material 806 is half of coax section dielectric material width 814 minus half of first antenna conductor width 218. For illustration, the depth of second antenna dielectric material 212 is 0.791 mm and second antenna dielectric width 222 is 2.197 mm.

Slot wall section 802 may be formed of a section of coaxial cable 102 having a slot length 824. Slot wall section 802 may include a slot center conductor 816 extending a length of slot wall section 802, a slot dielectric material 818 surrounding slot center conductor 816 extending a length of slot wall section 802, a slot conductive shield 820 surrounding coax section dielectric material 806 along the length of slot wall section 802, and a slot insulating jacket 822 surrounding slot conductive shield 820 along the length of slot wall section 802. Slot length 824 may be selected from a range defined between and inclusive of $0.1\lambda_0$ and $0.2\lambda_0$.

In the illustrative embodiment of FIG. 8, base 208 connects to coax section center conductor 804. First antenna dielectric material 210 connects to and extends from coax section dielectric material 806. Second antenna dielectric material 212 connects to and may extend from coax section dielectric material 806. Reflector wall 400 connects to and extends from coax section conductive shield 808. Third antenna dielectric material 214 connects to and extends from coax section insulating jacket 810.

In the illustrative embodiment of FIG. 8, slot center conductor 816 connects between coax section center conductor 804 and center conductor 200 of coaxial cable 102. Slot dielectric material 818 connects between coax section dielectric material 806 and dielectric material 202 of coaxial cable 102. Slot conductive shield 820 connects between coax section conductive shield 808 and conductive shield 204 of coaxial cable 102. Slot insulating jacket 822 connects between coax section insulating jacket 810 and insulating jacket 206 of coaxial cable 102.

A slot wall 826 is formed on a first side of base 208 that is opposite a second side from which reflector wall 400 extends from coax section conductive shield 808. Slot wall 826 is formed through a portion of slot conductive shield 820 to expose slot dielectric material 818 from a third angle 900 to a fourth angle 902 when projected into radial plane 234 in a manner similar to that described for first angle 506 and for second angle 508 except with reference to a first side wall 908 of slot wall 826 and to a second side wall 910 of slot wall 826, respectively. Slot wall 826 forms a slot 821. Slot 821 may be formed by removing a portion of slot conductive shield 820.

Third angle 900 is defined between up direction 500 and a third vector 904 that extends from axial direction 232 in radial plane 234 to first side wall 910 (shown referring to the first edge wall of reflector wall 400, which is parallel in the illustrative embodiment). Fourth angle 902 is defined between up direction 500 and a fourth vector 906 that extends from axial direction 232 in radial plane 234 to second side wall 908 (shown referring to the second edge wall of reflector wall 400, which is parallel in the illustrative embodiment). Up direction 500 is centered between third angle 900 and fourth angle 902. Slot angle 912 defines an angle between first vector 502 and second vector 504. Slot conductive shield 820 forms a wall between third vector 904 and fourth vector 906 and defines a total angle of 360° minus slot angle 912. In the illustrative embodiment of FIG. 9, slot angle 912 is equal to reflector slot angle 510 and is 90°. The total angle of the wall formed by slot conductive shield 820 is 270°.

Slot wall 826 has a slot wall width 828 between slot dielectric material 818 and slot insulating jacket 822. Slot wall width 828 may be selected as $\leq 0.1\lambda_0$. First angle 506, second angle 508, third angle 900, and fourth angle 902 are defined relative to a common axis, up direction 500, that is parallel to radial plane 234. In the illustrative embodiment of FIGS. 8 and 9, slot angle 912 and reflector slot angle 510 are equal though in an alternative embodiment, slot angle 912 and reflector slot angle 510 may not be equal.

Figure 10:
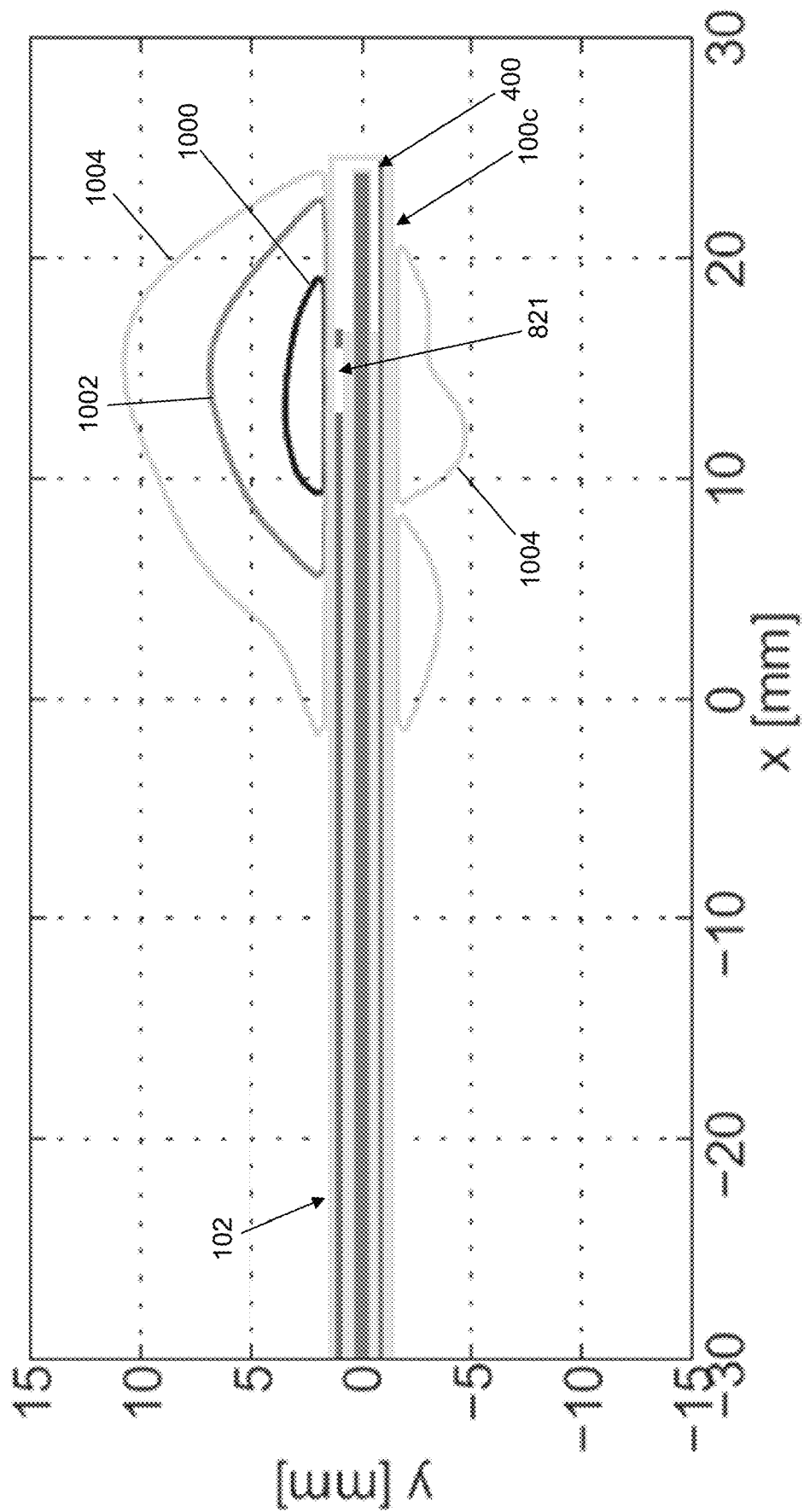
FIG. 10 shows a normalized SAR pattern of the third MWA antenna of FIGS. 8 and 9 in the x-y plane in accordance with an illustrative embodiment.

Referring to FIG. 10, a simulated SAR pattern formed by third antenna 100c is shown in accordance with an illustrative embodiment in the x-y plane, where y is in radial plane 234 and x is in axial direction 232. The SAR pattern was normalized to its associated maximum value. For operation at 7 GHz, third antenna 100c was selected to have antenna length 216 equal to 7 mm, reflector length 402 equal to 9 mm, slot length 824 equal to 4 mm, and coaxial section length 812 equal to 1 mm. The simulated results assumed egg white as the medium of operation of third antenna 100c. The dimensions of third antenna 100c were optimized in CST Studio to minimize the SAR values behind reflector wall 400.

A −5 decibel (dB) curve 1000 shows a SAR level reduced by 5 dB. A −15 dB curve 1002 shows a SAR level reduced by 15 dB. A −25 dB curve 1004 shows a SAR level reduced by 25 dB. Third antenna 100c and coaxial cable 102 are shown for reference. Third antenna 100c and coaxial cable 102 create a more asymmetric SAR pattern with a radiation that is decreased further behind (negative y-axis values) reflector wall 400 relative to the results shown in FIG. 6 for second antenna 100b. A −15 dB SAR contour is absent behind reflector wall 400 of third antenna 100c. A maximum normalized SAR value behind reflector wall 400 of third antenna 100c is reduced by 5 dB compared to second antenna 100b showing the efficacy of using slot 821 in enhancing a directionality of third antenna 100c. Moreover, comparing the SAR pattern of the axisymmetric monopole antenna shown in FIG. 3 for first antenna 100a and that shown in FIG. 10 for third antenna 100c reveals two important differences. First, third antenna 100c is capable of producing a highly directional SAR pattern. Second, third antenna 100c can suppress the unwanted currents flowing on an outer surface of insulating jacket 206 of coaxial cable 102 without a need for a coaxial balun. This eliminates the need for using a balun and thus, results in a reduction in an overall diameter and invasiveness of third antenna 100c.

Figure 11:
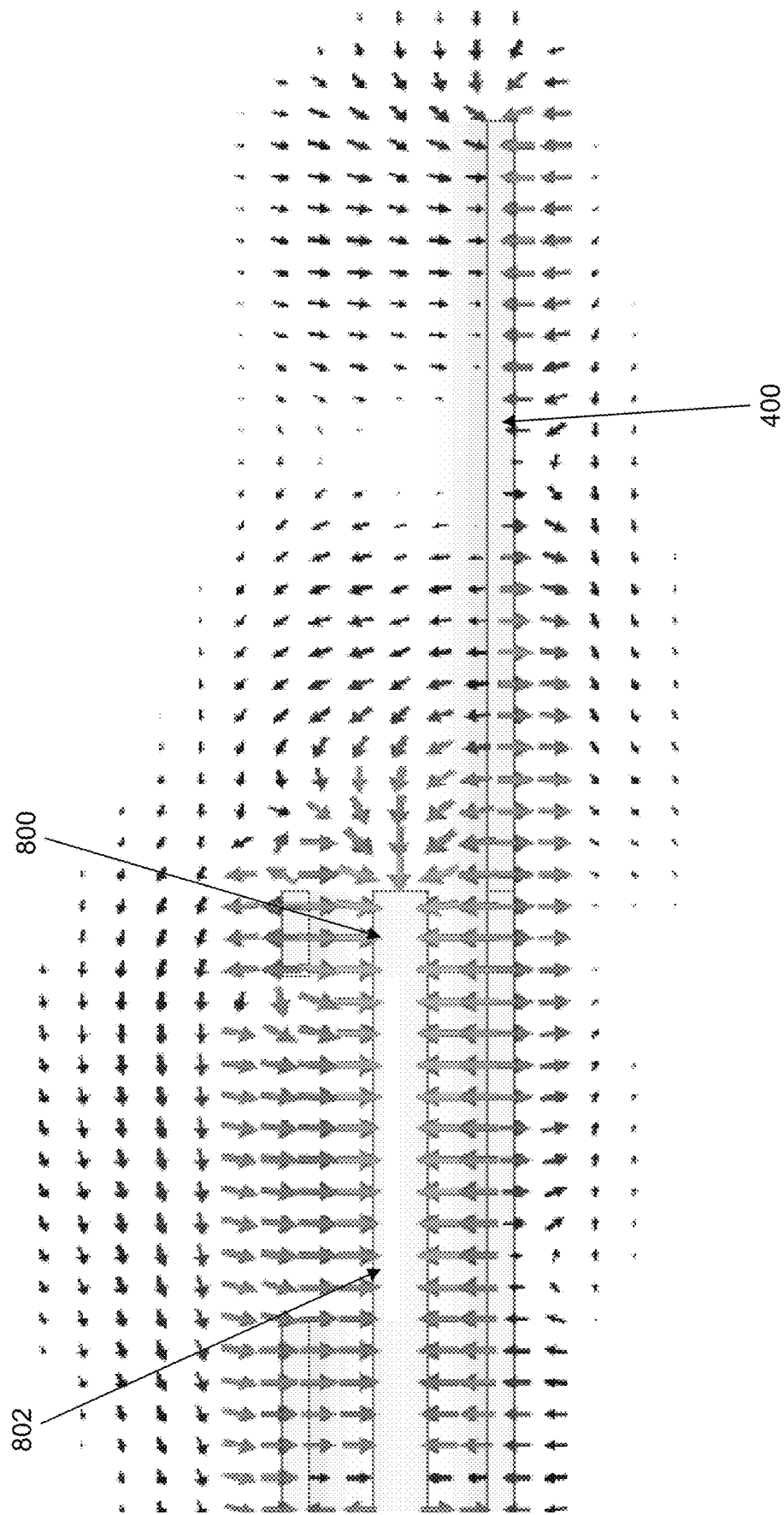
FIG. 11 shows a simulated electric field pattern of the third MWA antenna of FIGS. 8 and 9 in the x-y plane in accordance with an illustrative embodiment.

Referring to FIG. 11, a simulated electric field direction in a near field region formed by third antenna 100c operating at 7 GHz is shown in accordance with an illustrative embodiment in the x-y plane. The simulated electric field is shown for third antenna 100c with antenna length 216 selected as 0 mm, reflector length 402 selected as 9 mm, slot length 824 selected as 4 mm, coaxial section length 812 selected as 1 mm. The simulated electric field direction is shown using a normalized dB scale (with respect to its corresponding maximum value) for the electric field. A main radiation from third antenna 100c comes from the slot formed by slot wall section 802. As can be seen, the direction of the electric field below reflector wall 400 is opposite to that shown in FIG. 7 in a region in a vicinity of a tip of reflector wall 400.

Figure 12:
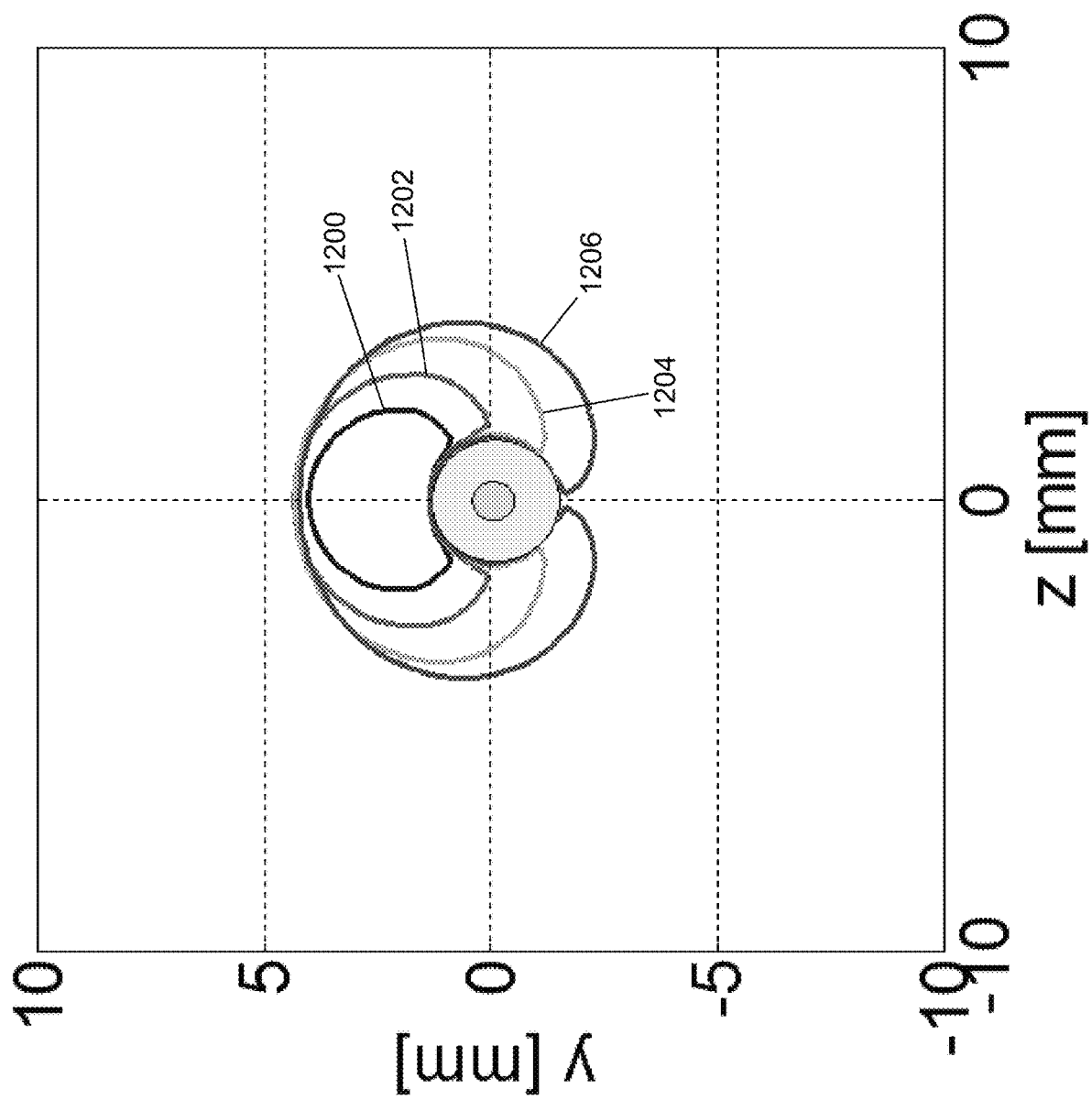
FIG. 12 shows −10 dB SAR patterns at a feed point to the third MWA antenna of FIGS. 8 and 9 in the x-z plane for slot arc lengths of 90°, 180°, 270°, and 350° in accordance with an illustrative embodiment.

Referring to FIG. 12, −10 dB SAR patterns at base 208 of third antenna 100c in the x-z plane are shown in accordance with an illustrative embodiment. A first curve 1200 shows a −10 dB SAR level for slot angle 912 and reflector slot angle 510 equal to 90° (slot wall 820 forming an angle of 270°). A second curve 1202 shows a −10 dB SAR level for slot angle 912 and reflector slot angle 510 equal to 180° (slot wall 820 forming an angle of 180°). A third curve 1204 shows a −10 dB SAR level for slot angle 912 and reflector slot angle 510 equal to 270° (slot wall 820 forming an angle of 90°). A fourth curve 1206 shows a −10 dB SAR level for slot angle 912 and reflector slot angle 510 equal to 350° (slot wall 820 forming an angle of 10°).

Figure 13:
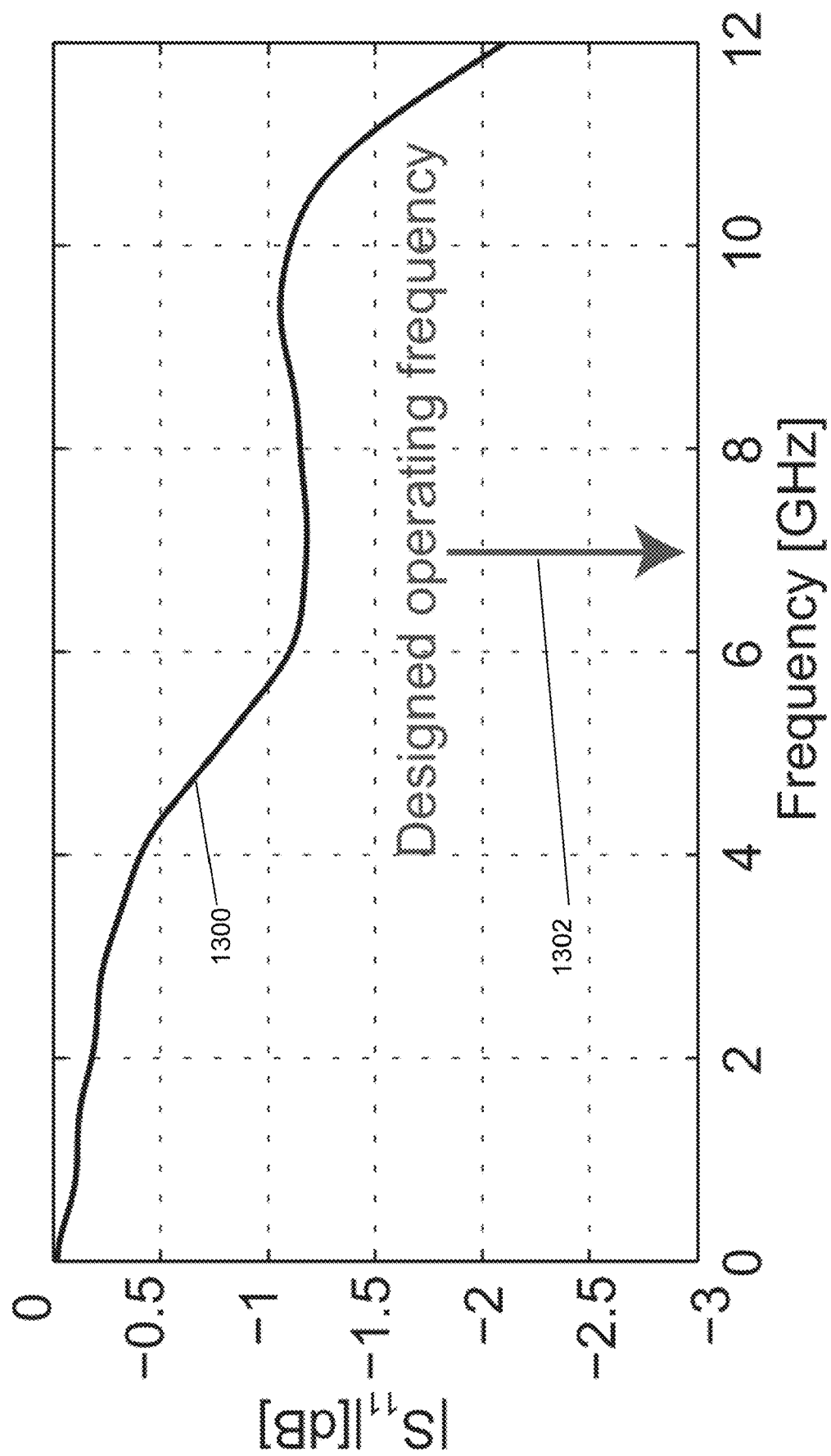
FIG. 13 shows a simulated reflection coefficient, $|S_{11}|$, of the third MWA antenna of FIGS. 8 and 9 without a matching network in accordance with an illustrative embodiment.

Referring to FIG. 13, a simulated reflection coefficient, $|S_{11}|$, curve 1300 of third antenna 100c without a matching network is shown in accordance with an illustrative embodiment. The presence of reflector wall 400 behind and in close proximity to antenna conductor 209 reduces a feed point impedance of third antenna 100c degrading the impedance matching. As shown at an operating frequency 1302 of 7 GHz, this low input impedance corresponds to an $|S_{11}|$ value of ~−1.17 dB. To solve this problem, an internal impedance matching structure can be employed.

Figure 14A:
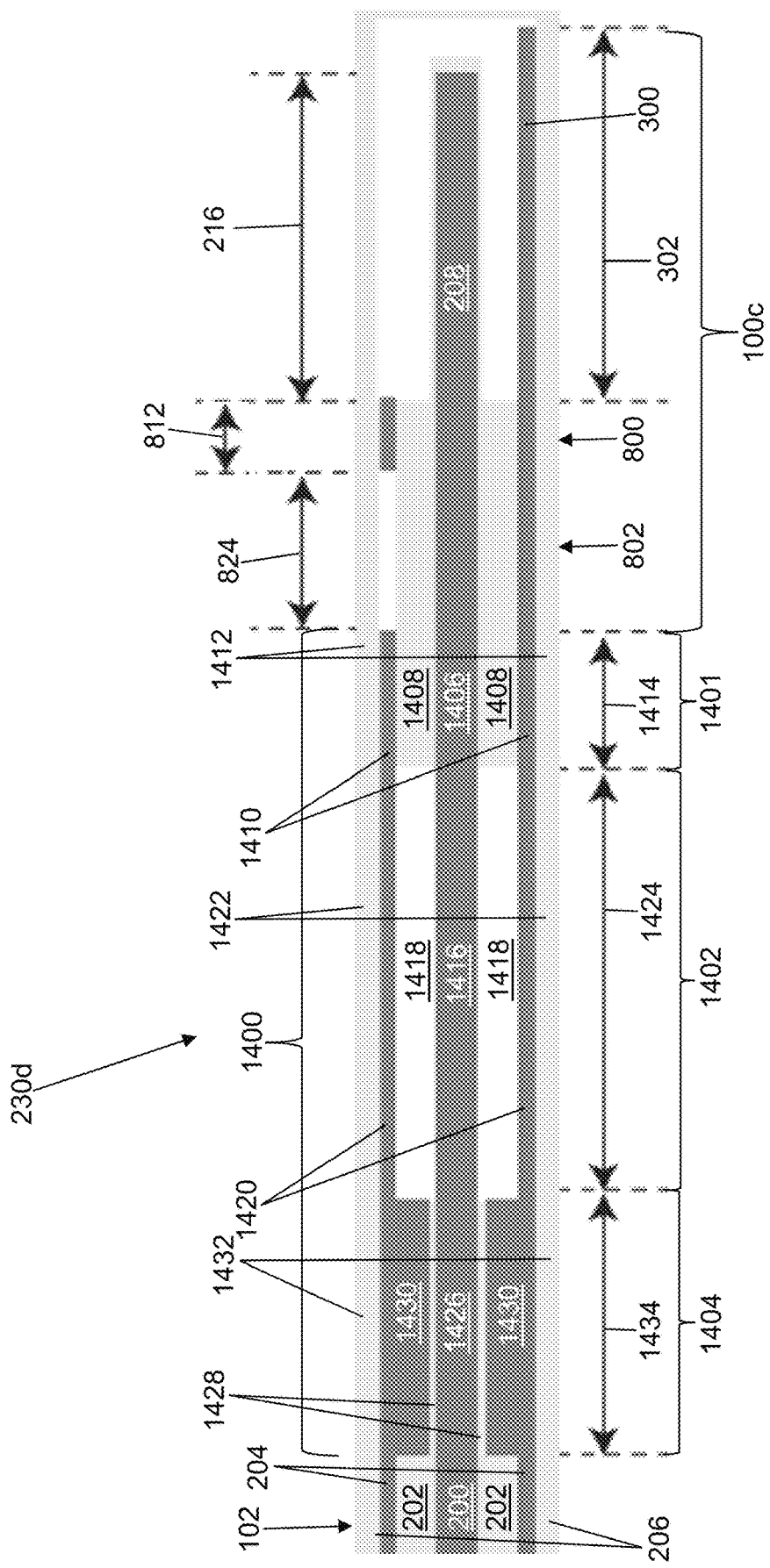
FIG. 14A depicts a side cross sectional view of the third MWA antenna of FIGS. 8 and 9 with a matching network in accordance with an illustrative embodiment.
Figure 14B:
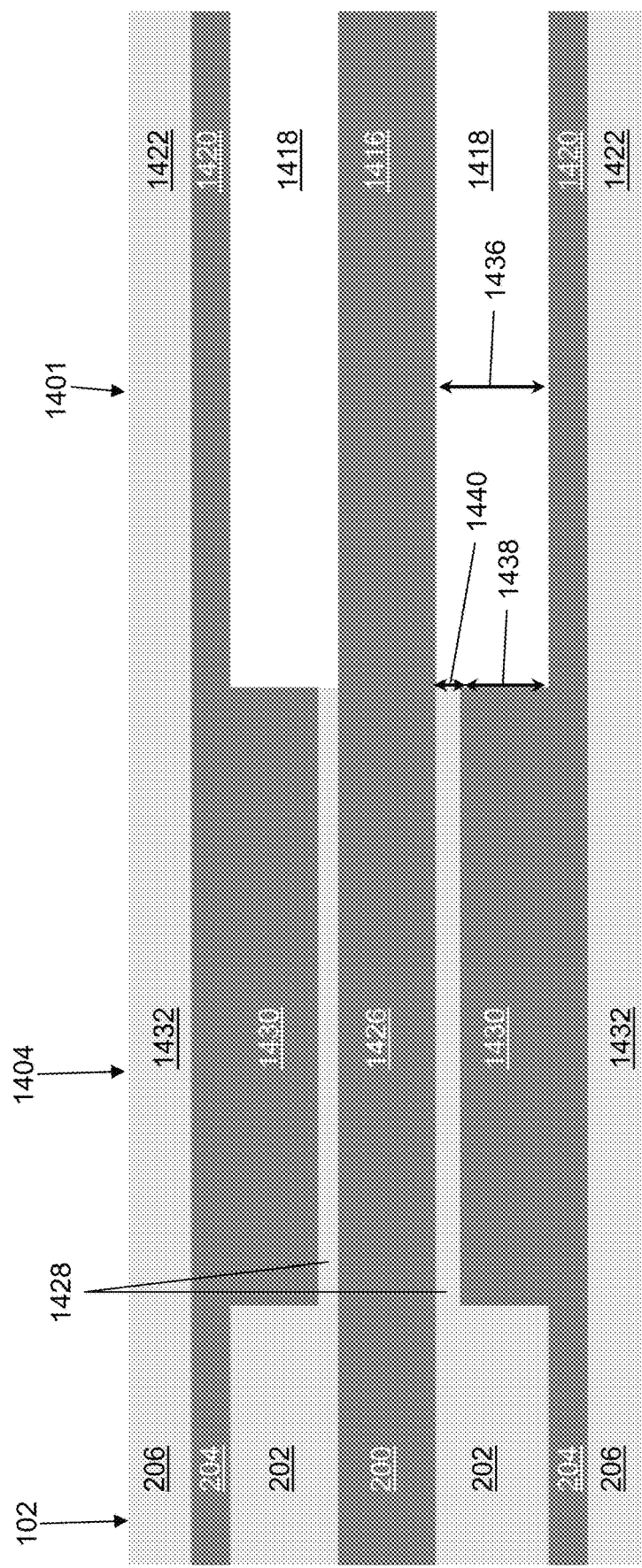
FIG. 14B depicts a zoomed, side cross sectional view of the matching network of FIG. 14A in accordance with an illustrative embodiment.

For example, referring to FIGS. 14A and 14B, a fourth antenna system 230d is shown in accordance with an illustrative embodiment. Fourth antenna system 230d may include coaxial cable 102, an impedance matching structure 1400, and third antenna 100c. Impedance matching structure 1400 is configured to match an impedance of coaxial cable 102 to an impedance of third antenna 100c. Impedance matching structure 1400 is connected between coaxial cable 102 and a proximal end of third antenna 100c.

Impedance matching structure 1400 may include a first low impedance section 1401, a high impedance section 1402, and a second low impedance section 1404. In the illustrative embodiment, first low impedance section 1401 is identical to coaxial cable 102. In another illustrative embodiment, first low impedance section 1401 is identical to second low impedance section 1404. Impedance matching structure 1400 may be formed from an extension of coaxial cable 102. High impedance section 1402 is connected between first low impedance section 1401 and second low impedance section 1404. First low impedance section 1401 is connected between high impedance section 1402 and third antenna 100c. Second low impedance section 1404 is connected between high impedance section 1402 and coaxial cable 102.

First low impedance section 1401 may be formed of a section of coaxial cable 102 having a first low impedance section length 1414. First low impedance section 1401 may include a first low impedance section center conductor 1406 extending a length of first low impedance section length 1414, a first low impedance section dielectric material 1408 surrounding first low impedance section center conductor 1406 extending a length of first low impedance section length 1414, a first low impedance section conductive shield 1410 surrounding first low impedance section dielectric material 1408 along the length of first low impedance section length 1414, and a first low impedance section insulating jacket 1412 surrounding first low impedance section conductive shield 1410 along the length of first low impedance section length 1414.

Second low impedance section 1404 may be formed of a section of coaxial cable 102 having a second low impedance section length 1434. Second low impedance section 1404 may include a second low impedance section center conductor 1426 extending a length of second low impedance section length 1434, a second low impedance section dielectric material 1428 surrounding second low impedance section center conductor 1426 extending a length of second low impedance section length 1434, a second low impedance section conductive shield 1430 surrounding second low impedance section dielectric material 1428 along the length of second low impedance section length 1434, and a second low impedance section insulating jacket 1432 surrounding second low impedance section conductive shield 1430 along the length of second low impedance section length 1434. Second low impedance section conductive shield 1430 has a conductor width 1438. Second low impedance section dielectric material 1428 has a dielectric width 1440.

High impedance section 1402 may be formed of a section of coaxial cable 102 having a high impedance section length 1424. High impedance section 1402 may include a high impedance section center conductor 1416 extending a length of high impedance section length 1424, a high impedance section dielectric material 1418 surrounding high impedance section center conductor 1416 extending a length of high impedance section length 1424, a high impedance section conductive shield 1420 surrounding high impedance section dielectric material 1418 along the length of high impedance section length 1424, and a high impedance section insulating jacket 1422 surrounding high impedance section conductive shield 1420 along the length of high impedance section length 1424.

In an illustrative embodiment, high impedance section 1402 is identical to first low impedance section 1401 except that first low impedance section dielectric material 1408 has been replaced with a different dielectric material that has a lower relative permittivity such as air. Second low impedance section 1404 may be formed by inserting a hollow copper tube in the region between center conductor 200 of coaxial cable 102 and outer conductor 204 of coaxial cable 102, effectively reducing the width of region 202. The hollow copper tube forms a new outer conductor with a reduced inner diameter.

High impedance section dielectric material 1418 has a width 1436 that may be equal to a width of first low impedance section dielectric material 1408. A sum of conductor width 1438 and dielectric width 1440 may be equal to width 1436 of high impedance section dielectric material 1418.

Removing low impedance section dielectric material 1408 reduces a capacitance per unit length of impedance matching structure 1400 and increases its characteristic impedance. A short transmission line with a high impedance can be modeled as a series inductor. On the other hand, second low impedance section 1404 may be implemented by decreasing an inner diameter of conductive shield 204 of coaxial cable 102 such that conductor width 1438 is larger for second low impedance section conductive shield 1430 than for conductive shield 204 of coaxial cable 102, which increases the capacitance per unit length of the line and decreases its characteristic impedance. A short section of a transmission line with a low characteristic impedance is equivalent to a parallel capacitor. Therefore, impedance matching structure 1400 is equivalent to a series inductor (high impedance section 1402) sandwiched by two parallel capacitors (first low impedance section 1401 and second low impedance section 1404). The values of a first capacitance for first low impedance section 1401, of an inductance for high impedance section 1402, and second capacitance for second low impedance section 1404 are chosen to provide an impedance match between third antenna 100c and coaxial cable 102.

Figure 15:
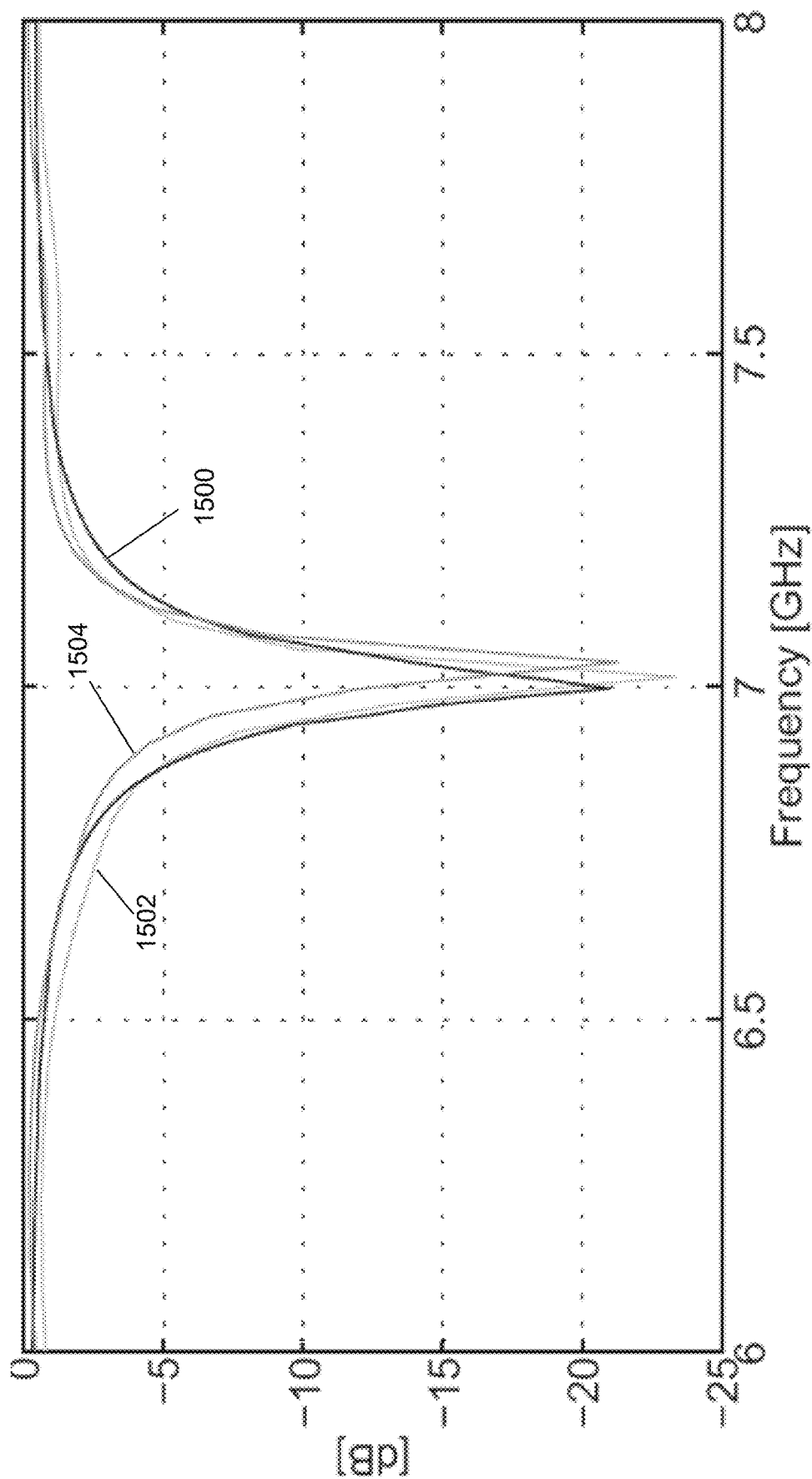
FIG. 15 shows a simulated and a measured reflection coefficient, $|S_{11}|$, pre-ablation and post-ablation of the third MWA antenna with the matching network of FIGS. 14A and 14B in accordance with an illustrative embodiment.

In an illustrative embodiment, first low impedance section length 1414, high impedance section length 1424, and second low impedance section length 1434 may be calculated using the parameters defined for third antenna 100c operating at 7 GHz and finely tuned using full wave EM simulations in CST Microwave Studio® or another EM simulation tool. Referring to FIG. 15, a simulated input impedance, $|S_{11}|$, curve 1500 of third antenna 100c with impedance matching structure 1400 is shown in accordance with an illustrative embodiment. First low impedance section length 1414 was selected as 4 mm, high impedance section length 1424 was selected as 12 mm, second low impedance section length 1434 was selected as 7 mm, and conductor width 1438 was selected as 0.898 mm computed using 0.5*(1.678−0.78).

Third antenna 100c was fabricated and used to perform ablation experiments in egg white. A signal generator (HP 8350B sweep oscillator) was used to produce a 7.05 GHz continuous-wave signal. The generated signal was fed to a power amplifier (IFI T186-50 TWT amplifier), the output of which was fed to impedance matching structure 1400 using a 40 centimeter (cm) long coaxial cable 102. Ablation experiments were conducted at a power level of 20 W for a duration of 5 minutes. During the experiments, a reflected power back towards the power amplifier was monitored. The maximum reflected power during the entire ablation procedure was observed to be less than one W indicating that third antenna 100c maintained a good impedance match throughout the entire ablation process as dielectric constant of the medium (egg white) changed.

A pre-ablation measured reflection coefficient, $|S_{11}|$, curve 1502 of third antenna 100, and a post-ablation measured reflection coefficient, $|S_{11}|$, curve 1504 of third antenna 100c are shown in FIG. 15. The small differences between simulated reflection coefficient, $|S_{11}|$, curve 1500, pre-ablation measured reflection coefficient, $|S_{11}|$, curve 1502, and post-ablation measured reflection coefficient, $|S_{11}|$, curve 1504 can be attributed to errors that mostly arise in fabrication of impedance matching structure 1400, as well as uncertainties in a precise value of a dielectric constant of egg white and the changes of the dielectric constant of the egg white that occur during ablation.

The results confirm that third antenna 100c is well-matched at 7.0 GHz using impedance matching structure 1400 because a low $|S_{11}|$ of ~−20 dB is obtained. Additionally, third antenna 100c has a relatively narrow bandwidth of ~1.8%, which is a fairly narrow bandwidth due to the large impedance mismatch. This, however, does not pose a practical limitation for using third antenna 100c in MWA applications because MWA is performed at a single frequency.

Figure 17:
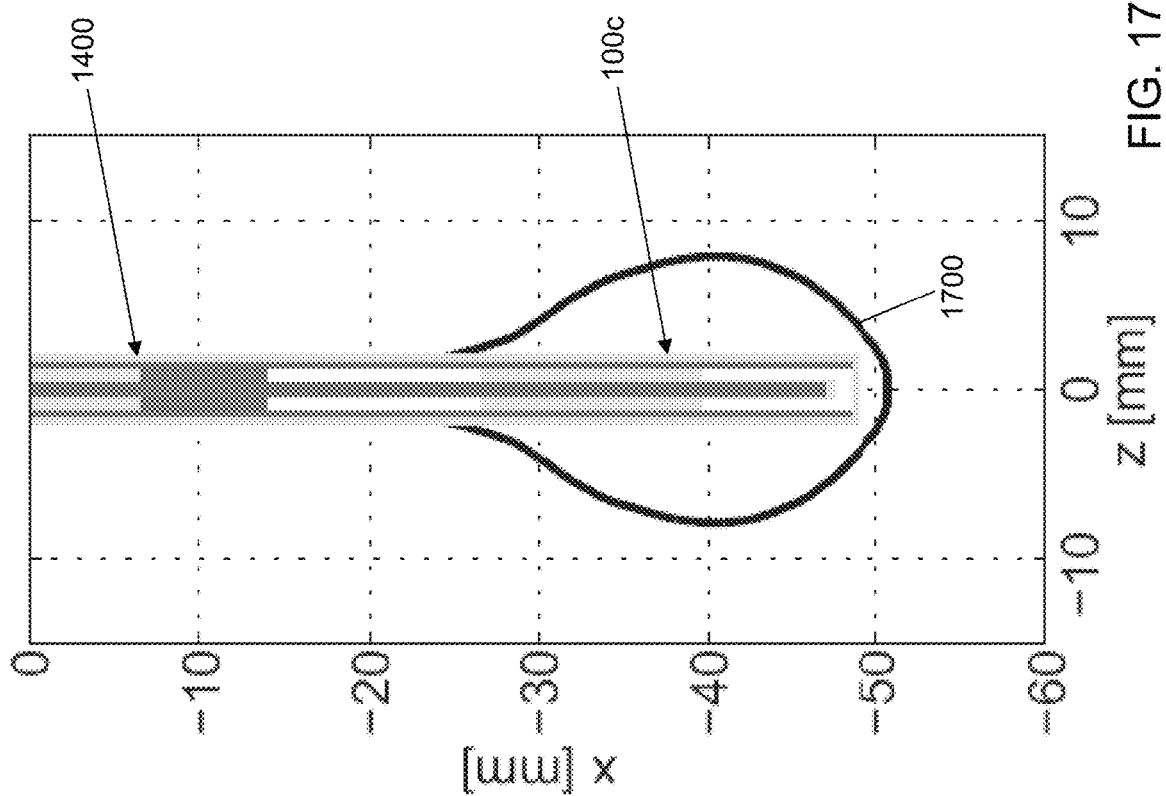
FIG. 17 shows a simulated ablation zone of the third MWA antenna of FIGS. 8 and 9 in the x-z plane in accordance with an illustrative embodiment.
Figure 16:
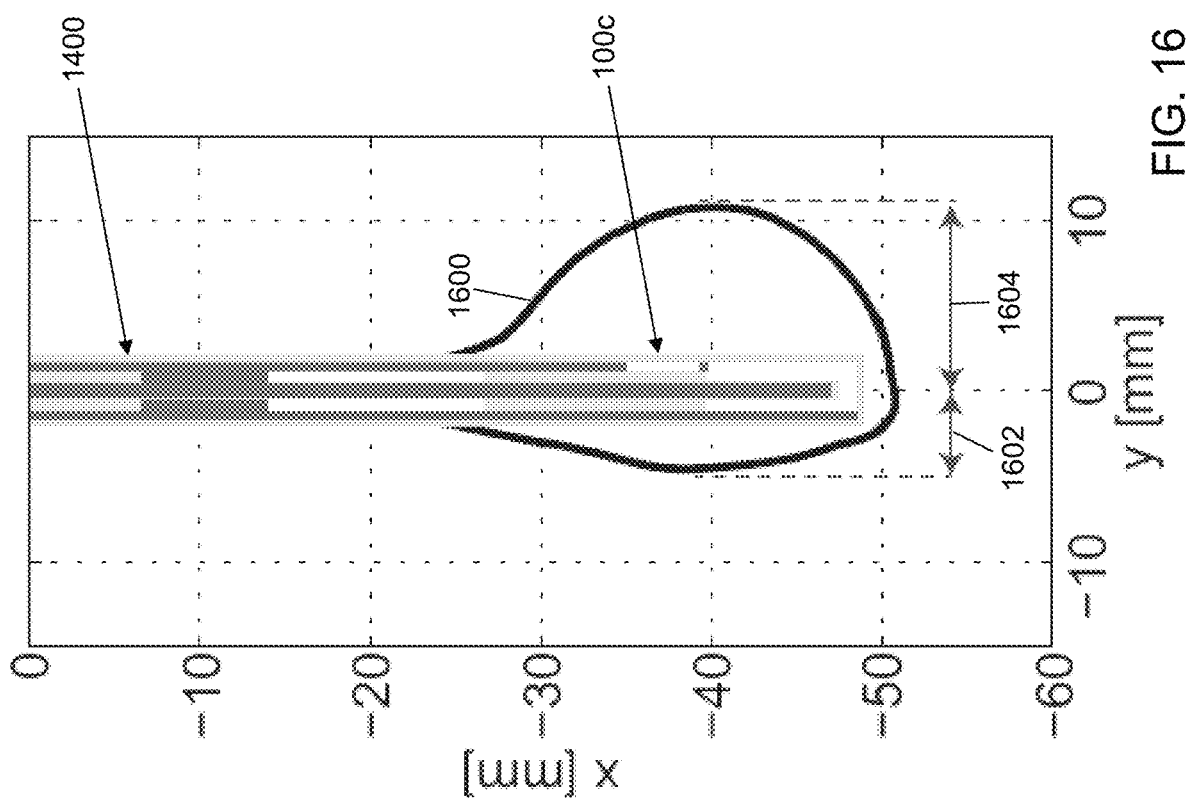
FIG. 16 shows a simulated ablation zone of the third MWA antenna of FIGS. 8 and 9 in the x-y plane in accordance with an illustrative embodiment.

Referring to FIG. 16, a simulated x-y ablation zone 1600 of third antenna 100c in the x-y plane in egg white at a power level of 20 W after 5 minutes of ablation is shown in accordance with an illustrative embodiment. Referring to FIG. 17, a simulated x-z ablation zone 1700 of third antenna 100c in the x-z plane in egg white at a power level of 20 W after 5 minutes of ablation in accordance with an illustrative embodiment. As shown in FIG. 16, simulated x-y ablation zone 1600 is highly directional in the x-y plane (the plane of asymmetry) while simulated x-z ablation zone 1700 is symmetric in the x-z plane. To quantify a degree of directionality of simulated x-y ablation zone 1600, a first distance 1602 is compared to a second distance 1604. First distance 1602 and second distance 1604 are the distances between the edges of simulated x-y ablation zone 1600 and a center of third antenna 100c on each side of base 208. A directionality ratio (DR) of 100% means a completely directional heating pattern while a value of 0% indicates a completely symmetric pattern. For simulated x-y ablation zone 1600, the DR values are 41% in the x-y plane and 0% and in the x-z plane.

Figure 18:
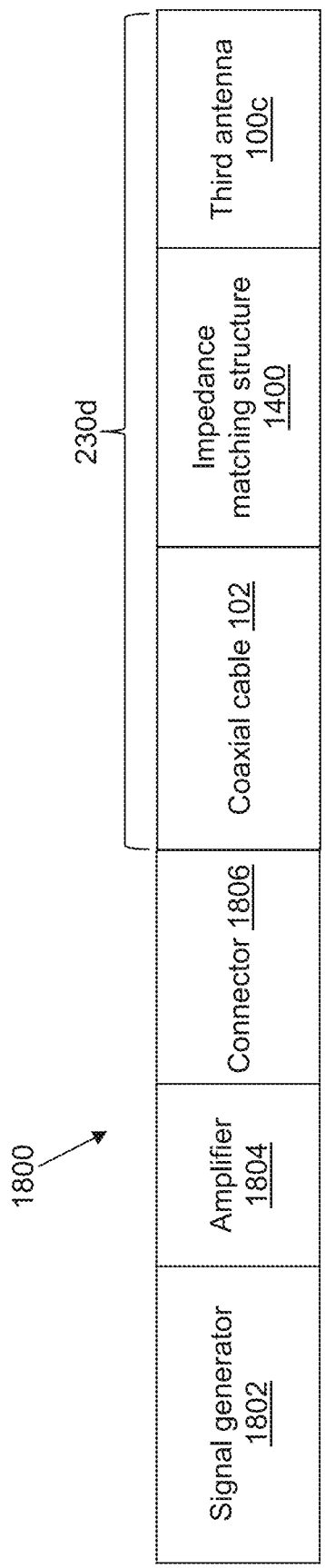
FIG. 18 depicts a block diagram of a MWA system incorporating the MWA antenna system of FIG. 1 in accordance with an illustrative embodiment.

Referring to FIG. 18, a block diagram of a MWA system 1800 is shown in accordance with an illustrative embodiment. MWA system 1800 may include a signal generator 1802, an amplifier 1804, a connector 1806, coaxial cable 102, and fourth antenna system 230d. Signal generator 1802 generates an analog signal at the operating frequency selected for third antenna 100c. A duty cycle of the analog signal may be controlled by signal generator 1802 based, for example, on an ablation zone size and heating rate. The analog signal may be amplified by amplifier 1804. Connector 1806 connects a second end of coaxial cable 102 opposite impedance matching structure 1400. The loss through coaxial cable 102 is considered when adjusting the output power level of amplifier 1804 for a desired input power level to third antenna 100c. Connector 1806 may be a coaxial connector designed to maintain the coaxial form across the connection and having the same impedance as coaxial cable 102.

Third antenna 100c exploits a reflector-backed monopole in combination with a semi-annular slot etched in the outer conductor of a feeding coaxial cable 102 to obtain highly directional SAR and heating patterns in which the SAR values in the backward region are 15 dB below the values in the forward region and the lateral expansion of the heating zone in the backward region is approximately 0.4 times that of the forward region. Third antenna 100c is also capable of producing compact SAR patterns and localized ablation zones without using a coaxial balun. The use of a reflector in close proximity to the radiating monopole deteriorates impedance matching, but can be resolved by using an impedance matching structure.

As understood by a person of skill in the art, at least some of the dimensions described herein are a function of the wavelength and/or characteristics of coaxial cable 102 selected for the MWA antenna system. Additionally, for simplicity of construction some of the width dimensions are illustrated as the same though this is not required. For example, center conductor 200, slot center conductor 816, coax section center conductor 804, and antenna conductor 209 are illustrated in FIG. 8 as having identical widths though this is not required.

Use of directional terms, such as top, bottom, right, left, front, back, upper, lower, horizontal, vertical, behind, etc. are merely intended to facilitate reference to the various surfaces of the described structures relative to the orientations introduced in the drawings and are not intended to be limiting in any manner unless otherwise indicated.

As used in this disclosure, the term "connect" includes join, unite, mount, couple, associate, insert, hang, hold, affix, attach, fasten, bind, paste, secure, bolt, screw, rivet, pin, nail, clasp, clamp, cement, fuse, solder, weld, glue, form over, slide together, layer, and other like terms. The phrases "connected on" and "connected to" include any interior or exterior portion of the element referenced. Elements referenced as connected to each other herein may further be integrally formed together. As a result, elements described herein as being connected to each other need not be discrete structural elements. The elements may be connected permanently, removably, or releasably.

As used in this disclosure, the term "mount" includes join, unite, connect, couple, associate, insert, hang, hold, affix, attach, fasten, bind, paste, secure, bolt, screw, rivet, pin, nail, clasp, clamp, cement, fuse, solder, weld, glue, form over, slide together, layer, and other like terms. The phrases "mounted on" and "mounted to" include any interior or exterior portion of the element referenced. These phrases also encompass direct connection (in which the referenced elements are in direct contact) and indirect connection (in which the referenced elements are not in direct contact, but are mounted together via intermediate elements). Elements referenced as mounted to each other herein may further be integrally formed together. As a result, elements described herein as being mounted to each other need not be discrete structural elements. The elements may be mounted permanently, removably, or releasably.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the disclosed subject matter has been presented for purposes of illustration and of description. It is not intended to be exhaustive or to limit the disclosed subject matter to the precise form disclosed, and modifications and variations are possible in light of the above teachings or may be acquired from practice of the disclosed subject matter. The embodiments were chosen and described in order to explain the principles of the disclosed subject matter and as practical applications of the disclosed subject matter to enable one skilled in the art to utilize the disclosed subject matter in various embodiments and with various modifications as suited to the particular use contemplated. It is intended that the scope of the disclosed subject matter be defined by the claims appended hereto and their equivalents.

What is claimed is:

1. An antenna system comprising:
 a coaxial cable comprising
  a center conductor extending a length of the coaxial cable;
  a dielectric material surrounding the center conductor along the length of the coaxial cable; and
  a conductive shield surrounding the dielectric material along the length of the coaxial cable;
 an antenna comprising
  a base connected to the center conductor on a first side of the base; and
  an antenna conductor connected to the base on a second side of the base opposite the first side, wherein the antenna conductor extends in an axial direction from the second side of the base, wherein a radial plane through the base is perpendicular to the axial direction;
 a reflector wall formed of a conductive material connected to the conductive shield to extend in the axial direction, wherein the reflector wall is separated from the antenna conductor by a second dielectric material in a radial direction relative to the antenna conductor, wherein the reflector wall is curved partially around the antenna conductor in the radial direction between a first angle and a second angle when projected into the radial plane; and
 a slot wall formed through a portion of the conductive shield to expose the dielectric material between a third angle and a fourth angle when projected into the radial plane, wherein the slot wall is separated from the center conductor by the dielectric material in the radial direction relative to the center conductor,
 wherein the first angle, the second angle, the third angle, and the fourth angle are defined relative to a common axis parallel to the radial plane, wherein the first angle is equal to the third angle, and the second angle is equal to the fourth angle.

2. The antenna system of claim 1, wherein the antenna is a monopole antenna.

3. The antenna system of claim 1, wherein the reflector wall has a reflector length in the axial direction defined from the radial plane that is greater than or equal to an antenna length of the antenna conductor in the axial direction defined from the radial plane.

4. The antenna system of claim 3, wherein the antenna length is $0.25\lambda$, where $\lambda$ is a wavelength at an operating frequency of a signal carried by the center conductor in a medium in which the antenna is selected to operate.

5. The antenna system of claim 3, wherein the reflector length is selected from a range defined between and inclusive of $0.25\lambda$ and $0.4\lambda$, where $\lambda$ is a wavelength at an operating frequency of a signal carried by the center conductor in a medium in which the antenna is selected to operate.

6. The antenna system of claim 1, wherein a distance defined from the radial plane to a closest end of the slot wall is selected from a range defined between and inclusive of $0.004\lambda$ and $0.1\lambda$, where $\lambda$ is a wavelength at an operating frequency of a signal carried by the center conductor in a medium in which the antenna is selected to operate.

7. The antenna system of claim 6, wherein the operating frequency is greater than or equal to 500 megahertz and less than or equal to 30 gigahertz.

8. The antenna system of claim 1, wherein a length of the slot wall defined parallel to the axial direction is selected from a range defined between and inclusive of $0.01\lambda$ and $0.25\lambda$, where $\lambda$ is a wavelength at an operating frequency of a signal carried by the center conductor in a medium in which the antenna is selected to operate.

9. The antenna system of claim 1, wherein an angular difference between the first angle and the second angle in the radial plane is between 10 degrees and 350 degrees.

10. The antenna system of claim 1, wherein an angular difference between the third angle and the fourth angle in the radial plane is between 10 degrees and 350 degrees.

11. The antenna system of claim 1, wherein the second dielectric material includes a coating on the antenna conductor.

12. The antenna system of claim 11, wherein the second dielectric material further includes air between the coating and the reflector wall.

13. The antenna system of claim 1, wherein an insulating material surrounds the conductive shield along the length of the coaxial cable and the reflector wall, covers a slot formed by the slot wall, and covers a reflector slot formed by the reflector wall.

14. The antenna system of claim 1, wherein the base and the antenna conductor are extensions of the center conductor of the coaxial cable.

15. The antenna system of claim 1, wherein the reflector wall is an extension of the conductive shield of the coaxial cable.

16. The antenna system of claim 1, further comprising:
an impedance matching structure formed in the coaxial cable, the impedance matching structure comprising
a section of the center conductor along a length of the impedance matching structure;
a second dielectric material surrounding the section of the center conductor along the length of the impedance matching structure; and
a second conductive shield surrounding the second dielectric material along the length of the impedance matching structure up to an end of the slot wall farthest from the base;
wherein the impedance matching structure is configured to match an impedance of the coaxial cable to an impedance of the antenna.

17. The antenna system of claim 16, wherein the impedance matching structure includes a first low impedance section, a second low impedance section, and a high impedance section between the first low impedance section and the second low impedance section.

18. The antenna system of claim 17, wherein the dielectric material in the high impedance section is different than the dielectric material in the first low impedance section and the dielectric material in the second low impedance section.

19. The antenna system of claim 17, wherein the first low impedance section is positioned between the high impedance section and the slot wall in the axial direction and is identical to the coaxial cable.

20. A microwave ablation system comprising:
an antenna system comprising
a coaxial cable comprising
a center conductor extending a length of the coaxial cable;
a dielectric material surrounding the center conductor along the length of the coaxial cable; and
a conductive shield surrounding the dielectric material along the length of the coaxial cable;
an antenna comprising
a base connected to the center conductor on a first side of the base; and
an antenna conductor connected to the base on a second side of the base opposite the first side, wherein the antenna conductor extends in an axial direction from the second side of the base, wherein a radial plane through the base is perpendicular to the axial direction;
a reflector formed of a conductive material connected to the conductive shield to extend in the axial direction, wherein the reflector is separated from the antenna conductor by a second dielectric material in a radial direction relative to the antenna conductor, wherein the reflector is curved partially around the antenna conductor in the radial direction between a first angle and a second angle when projected into the radial plane; and
a slot wall formed through a portion of the conductive shield to expose the dielectric material between a third angle and a fourth angle when projected into the radial plane, wherein the slot wall is separated from the center conductor by the dielectric material in the radial direction relative to the center conductor,
wherein the first angle, the second angle, the third angle, and the fourth angle are defined relative to a common axis parallel to the radial plane, wherein the first angle is equal to the third angle, and the second angle is equal to the fourth angle;
a signal generator configured to generate a signal at a selected operating frequency; and
a connector configured to connect a second end of the coaxial cable opposite the base of the antenna to the signal generator to receive the generated signal.

* * * * *

UNITED STATES PATENT AND TRADEMARK OFFICE
CERTIFICATE OF CORRECTION

PATENT NO. : 11,058,487 B2  
APPLICATION NO. : 15/454170  
DATED : July 13, 2021  
INVENTOR(S) : Nader Behdad et al.

Page 1 of 1

It is certified that error appears in the above-identified patent and that said Letters Patent is hereby corrected as shown below:

In the Specification

Column 4, Line 39:
Delete the phrase "$\lambda_2 = c/f_o$." and replace with --$\lambda_o = c/f_o$--.

Column 4, Line 57:
Delete the phrase "$0.252\lambda_o$." and replace with --$0.25\lambda_o$--.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*